(12) United States Patent
Looby et al.

(10) Patent No.: US 10,301,358 B2
(45) Date of Patent: May 28, 2019

(54) COLLAGEN IMAGING COMPOSITIONS

(71) Applicant: Collagen Medical, LLC, Boston, MA (US)

(72) Inventors: Richard J. Looby, Reading, MA (US); Peter D. Caravan, Cambridge, MA (US); Thomas J. McMurry, Winchester, MA (US)

(73) Assignee: Collagen Medical, LLC, Boston, MA (US)

( * ) Notice: Subject to any disclaimer, the term of this patent is extended or adjusted under 35 U.S.C. 154(b) by 177 days.

(21) Appl. No.: 15/196,626

(22) Filed: Jun. 29, 2016

(65) Prior Publication Data
US 2016/0376319 A1 Dec. 29, 2016

Related U.S. Application Data

(60) Provisional application No. 62/186,164, filed on Jun. 29, 2015.

(51) Int. Cl.
C07K 7/08 (2006.01)
A61K 49/14 (2006.01)
A61K 49/08 (2006.01)

(52) U.S. Cl.
CPC .............. C07K 7/08 (2013.01); A61K 49/085 (2013.01); A61K 49/14 (2013.01)

(58) Field of Classification Search
CPC .................................................. A61K 49/00
See application file for complete search history.

(56) References Cited

U.S. PATENT DOCUMENTS

| | | | |
|---|---|---|---|
| 4,647,447 A | 3/1987 | Gries et al. | |
| 5,155,224 A | 10/1992 | Rocklage et al. | |
| 6,991,775 B2 | 1/2006 | Koerner et al. | |
| 8,034,898 B2 | 10/2011 | Caravan et al. | |
| 2008/0044360 A1* | 2/2008 | Caravan | A61B 5/055 424/9.341 |
| 2008/0044380 A1 | 2/2008 | Bachand et al. | |
| 2011/0110866 A1* | 5/2011 | Chilkoti | A61K 49/085 424/9.34 |

FOREIGN PATENT DOCUMENTS

| | | |
|---|---|---|
| WO | WO 1996/23526 | 8/1996 |
| WO | WO 2001/08712 | 2/2001 |
| WO | WO 2001/09188 | 2/2001 |

OTHER PUBLICATIONS

Abd-Elgaliel et al. Exploring the structural requirements of collagen-binding peptides, Biopolymers, 100, 167-173. (Year: 2013).*
"A short guide to abbreviations and their use in peptide science," Journal of Peptide Science, 1999, vol. 5, pp. 465-471.
Hutson et al., "Liquid chromatographic determination of hydroxyproline in tissue samples," Journal of Chromatography B, vol. 791, 2003, pp. 247-430.
International Preliminary Report on Patentability, in International Application No. PCT/US2016/40106, dated Jan. 2, 2018, 9 pages.
U.S. Appl. No. 09/778,585, filed Feb. 7, 2001, Stefancik et al.
U.S. Appl. No. 10/209,416, filed Jul. 30, 2002, Weisskoff et al.
U.S. Appl. No. 10/209,183, filed Jul. 30, 2002, Zhang et al.
Caravan et al., "Collagen-targeted MRI contrast agent for molecular imaging of fibrosis," Angewandte Chemie International Edition, Sep. 25, 2007, vol. 46, No. 43, pp. 8181-8173.
Cerqueira et al., Standardized myocardial segmentation and nomenclature for tomographic imaging of the heart, Circulation, Jan. 29, 2002, vol. 105, pp. 539-542.
Helm et al., "Postinfarction myocardial scarring in mice: molecular magnetic resonance imaging with use of a collagen-targeting contrast agent," Radiology, Jun. 2008, vol. 247 No. 3, pp. 788-796.
International Search Report and Written Opinion in International Application No. PCT/US2016/40106, dated Nov. 17, 2016, 12 pages.
Kolodziej et al., "Peptide optimization and conjugation strategies in the development of molecularly targeted magnetic resonance imaging contrast agents," Methods in Molecular Biology, 2013, vol. 1088, pp. 185-211.
Rockey et al., Noninvasive measures of liver fibrosis, Hepatology, Feb. 2006, vol. 43, pp. S113-S120.
Spuentrup et al., "Molecular Magnetic Resonance Imaging of Myocardial Perfusion with EP-3600, a Collagen-Specific Contrast Agent: Initial Feasibility Study in a Swine Model", Circulation, Journal of the American Heart Association, 2009, pp. 1768-1775.
Thomsen, Nephrogenic systemic fibrosis, History and Epidemiology, Radiologic Clinics, Sep. 2009, vol. 47, No. 5, pp. 827-831.
Virmani et al.,"The Pathology of Unstable Coronary Lesions," Journal of Interventional Cardiology, 2002, vol. 15, No. 6, pp. 439-446.
Wagner et al., Contrast-enhanced MRI and routine single photon emission computed tomography (SPECT) perfusion imaging for detection of subendocardial myocardial infarcts: an imaging study, Lancet, 2003, vol. 361, pp. 374-379.

\* cited by examiner

*Primary Examiner* — Michael G. Hartley
*Assistant Examiner* — Jagadishwar R Samala
(74) *Attorney, Agent, or Firm* — Fish & Richardson P.C.

(57) ABSTRACT

Compounds and methods for imaging and/or assessing collagen are described. The compounds can include collagen binding peptides.

10 Claims, 15 Drawing Sheets

Specification includes a Sequence Listing.

Figure 1. Chemical structure of Compound ID No. 1
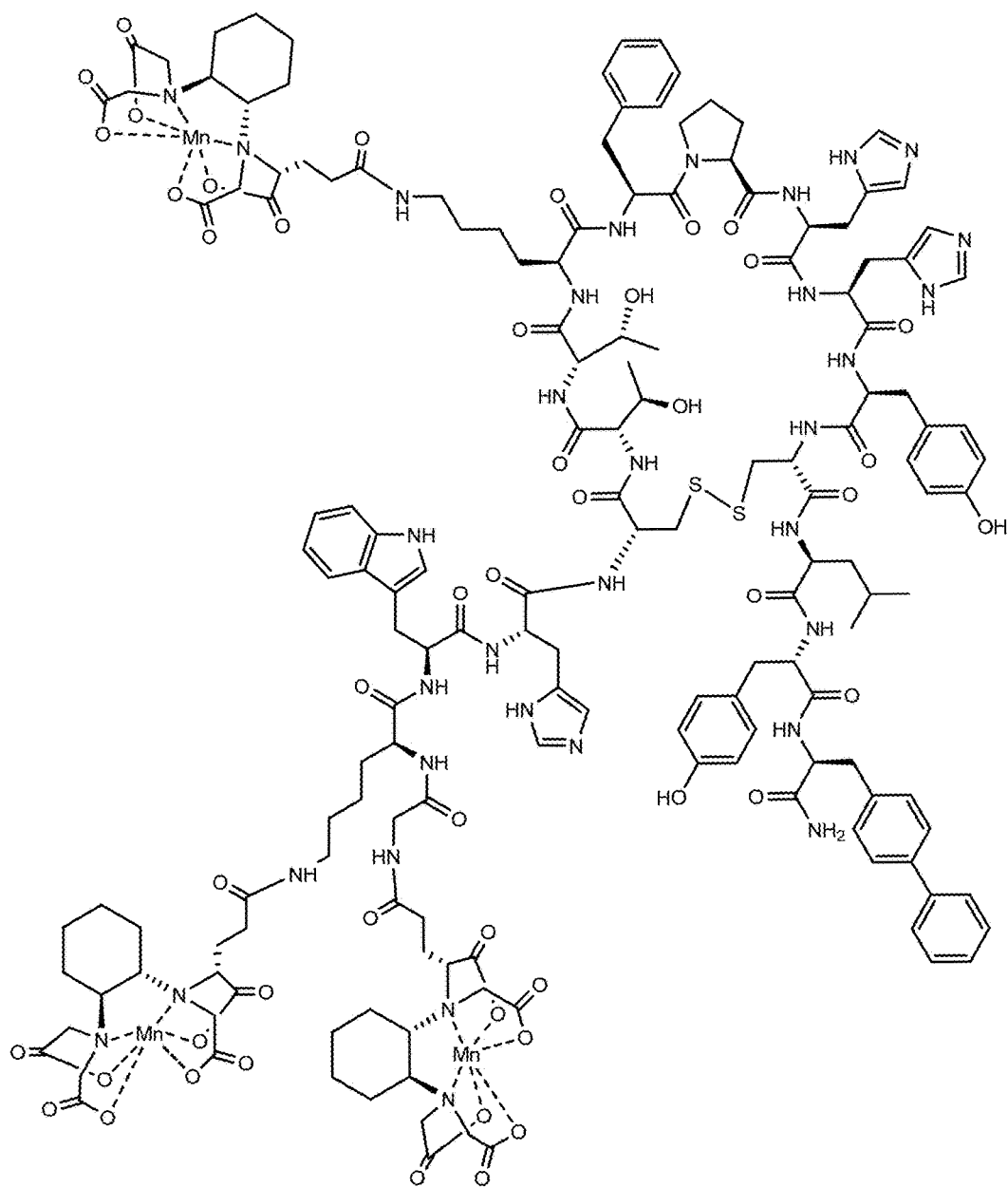

Figure 2. Chemical structure of Compound ID No. 2
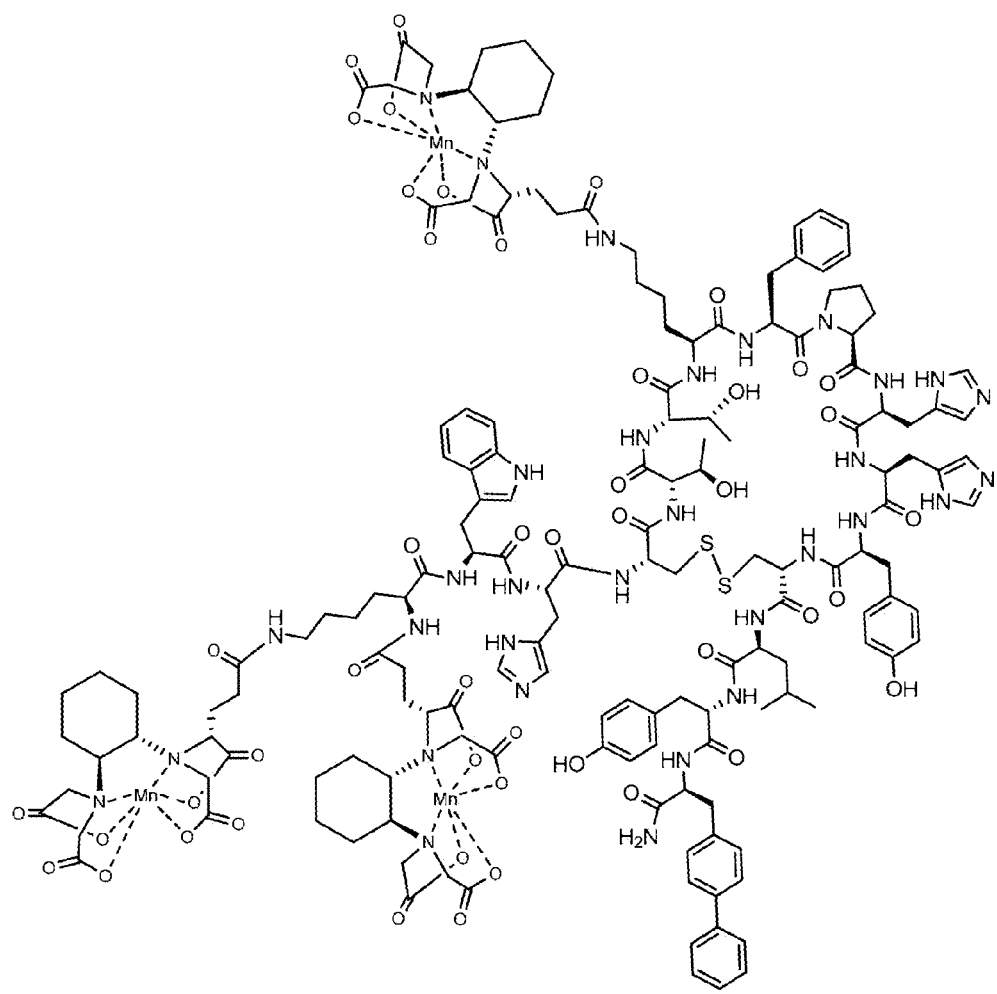

Figure 3. Chemical structure of Compound ID No. 3
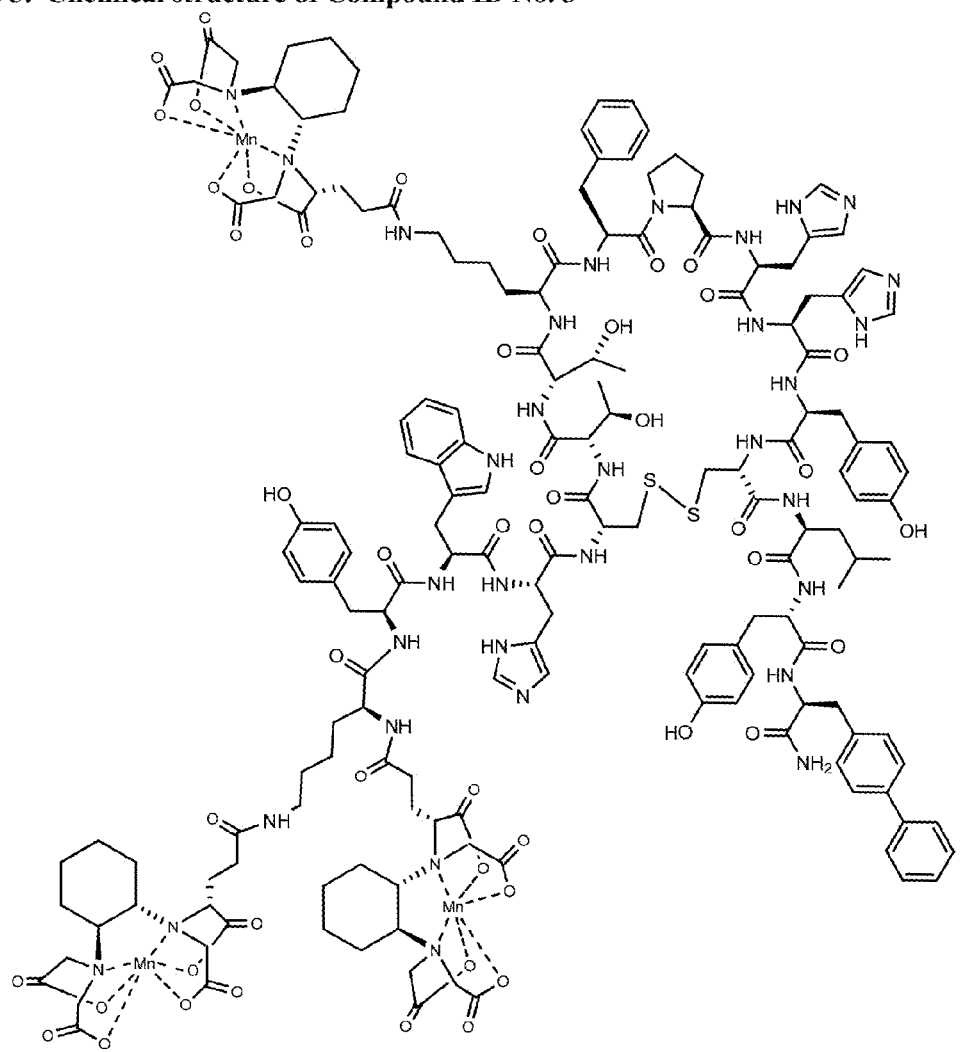

Figure 4. Chemical structure of Compound ID No. 4
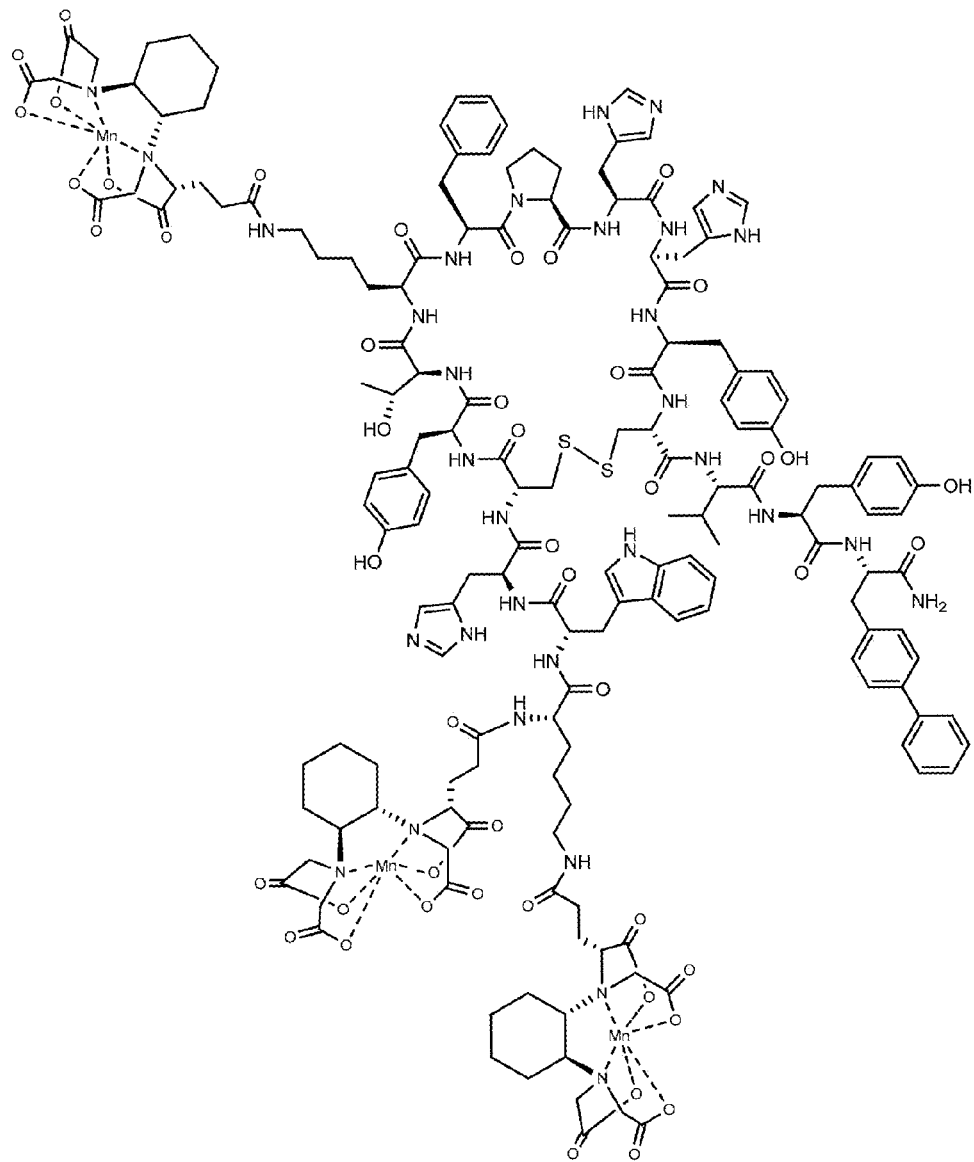

Figure 5. Chemical structure of Compound ID No. 5
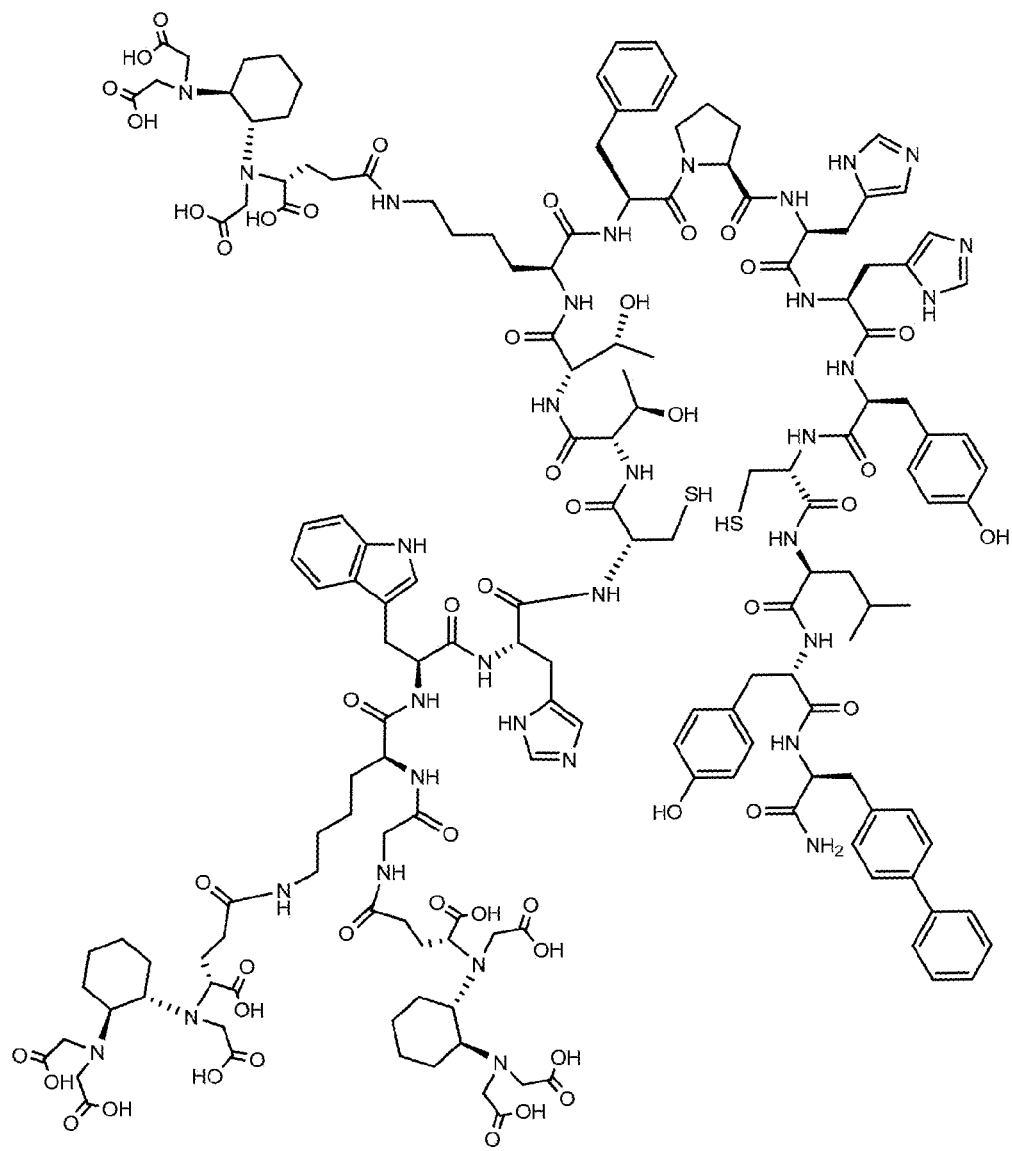

Figure 6. Chemical structure of Compound ID No. 6
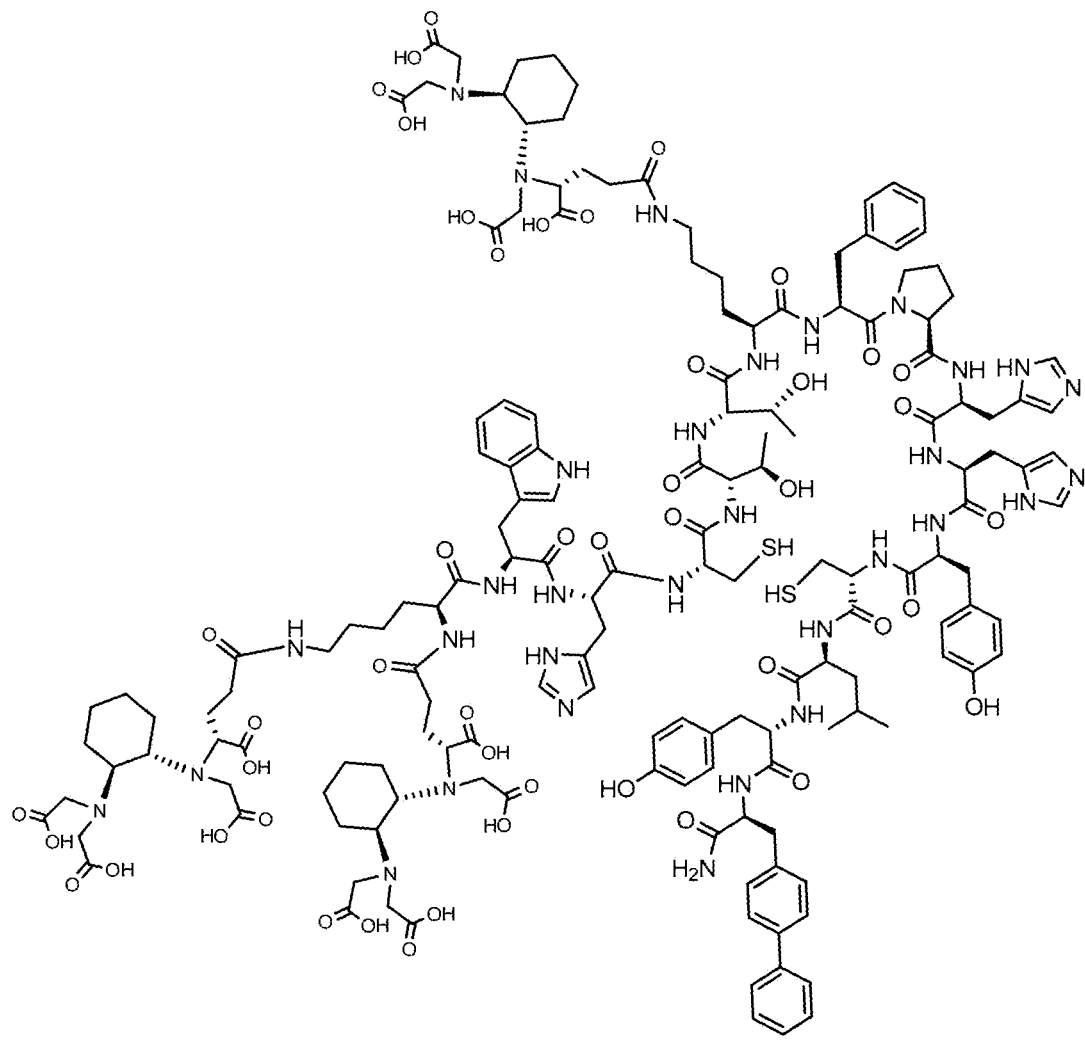

Figure 7. Chemical structure of Compound ID No. 7
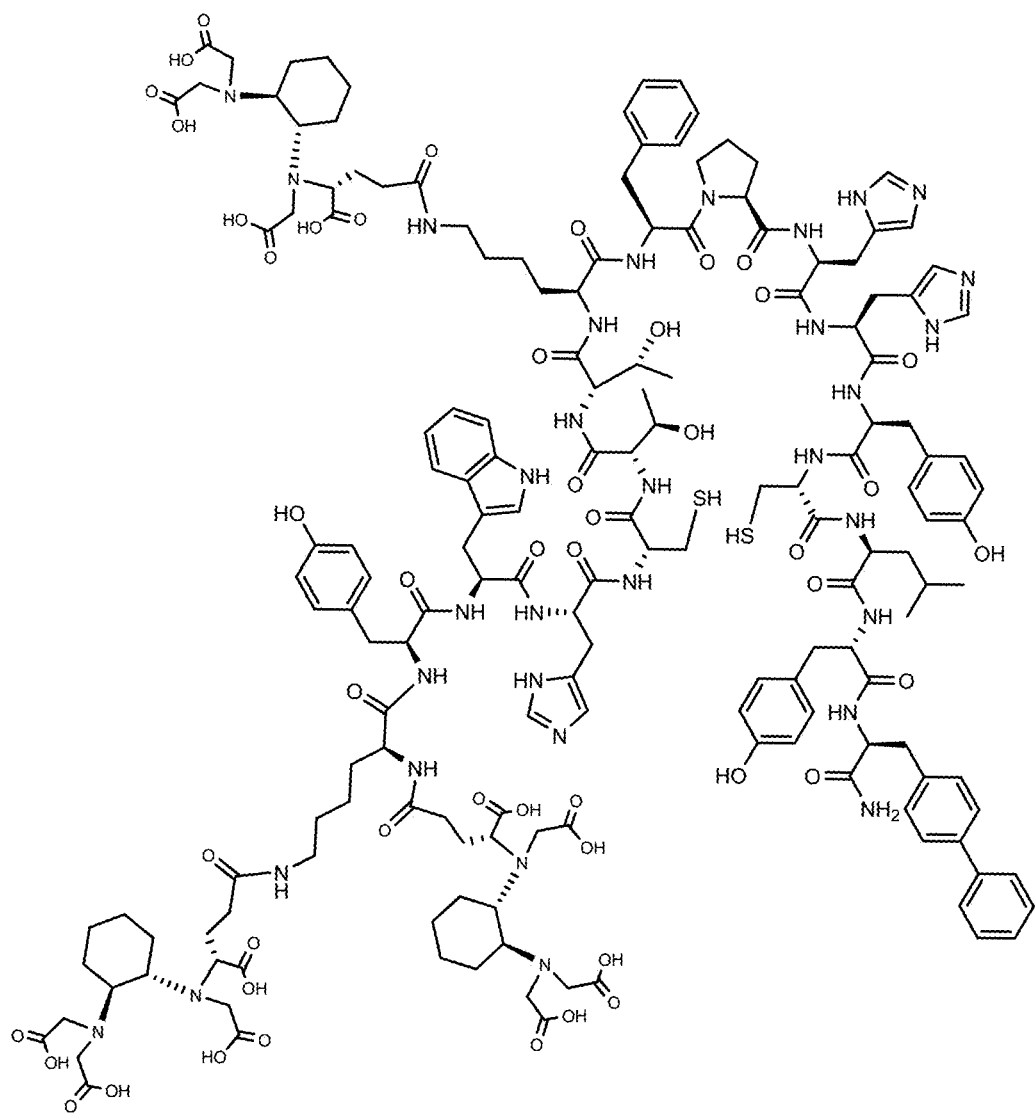

Figure 8. Chemical structure of Compound ID No. 8
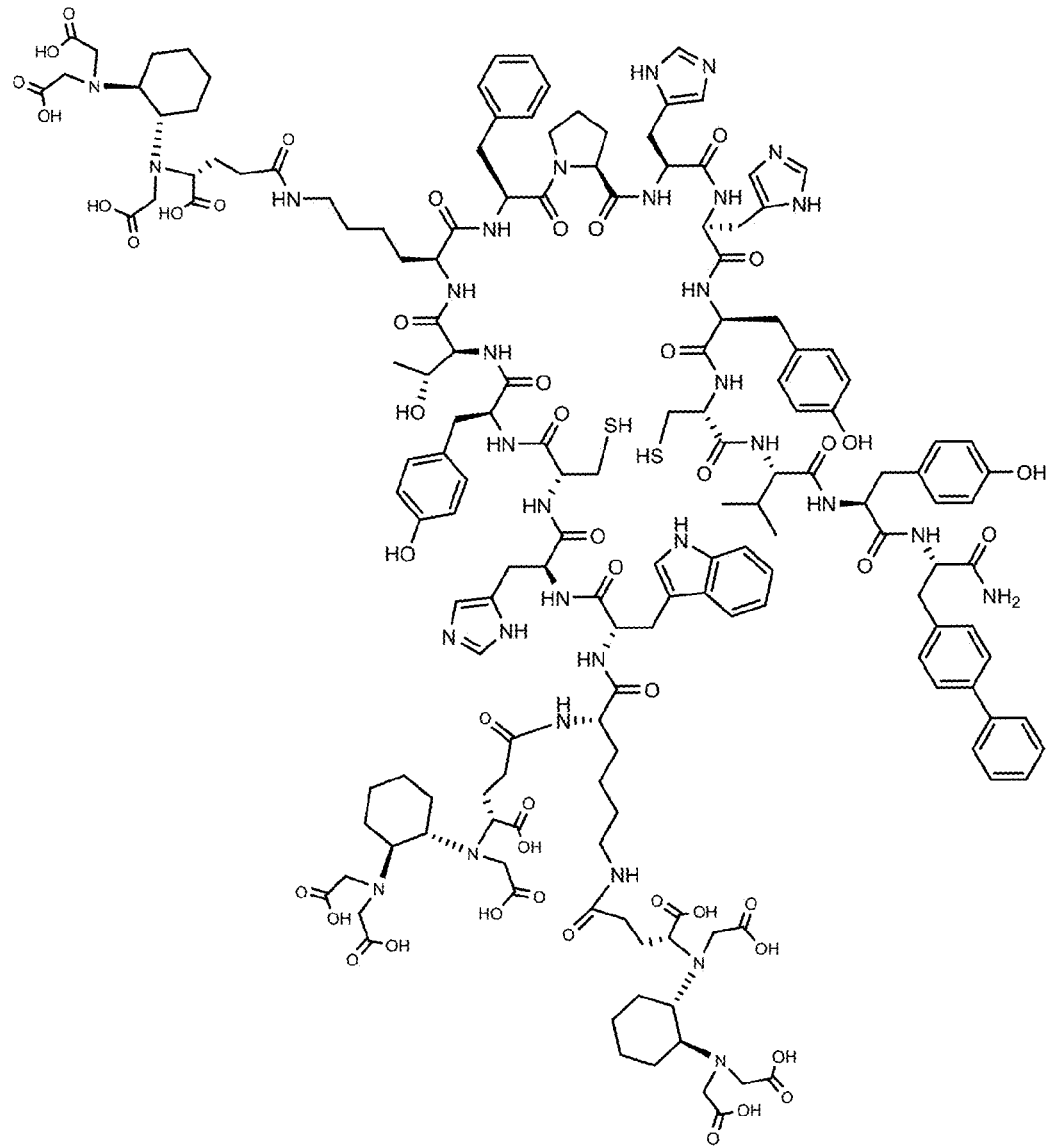

Figure 9. Chemical structure of Compound ID No. 9
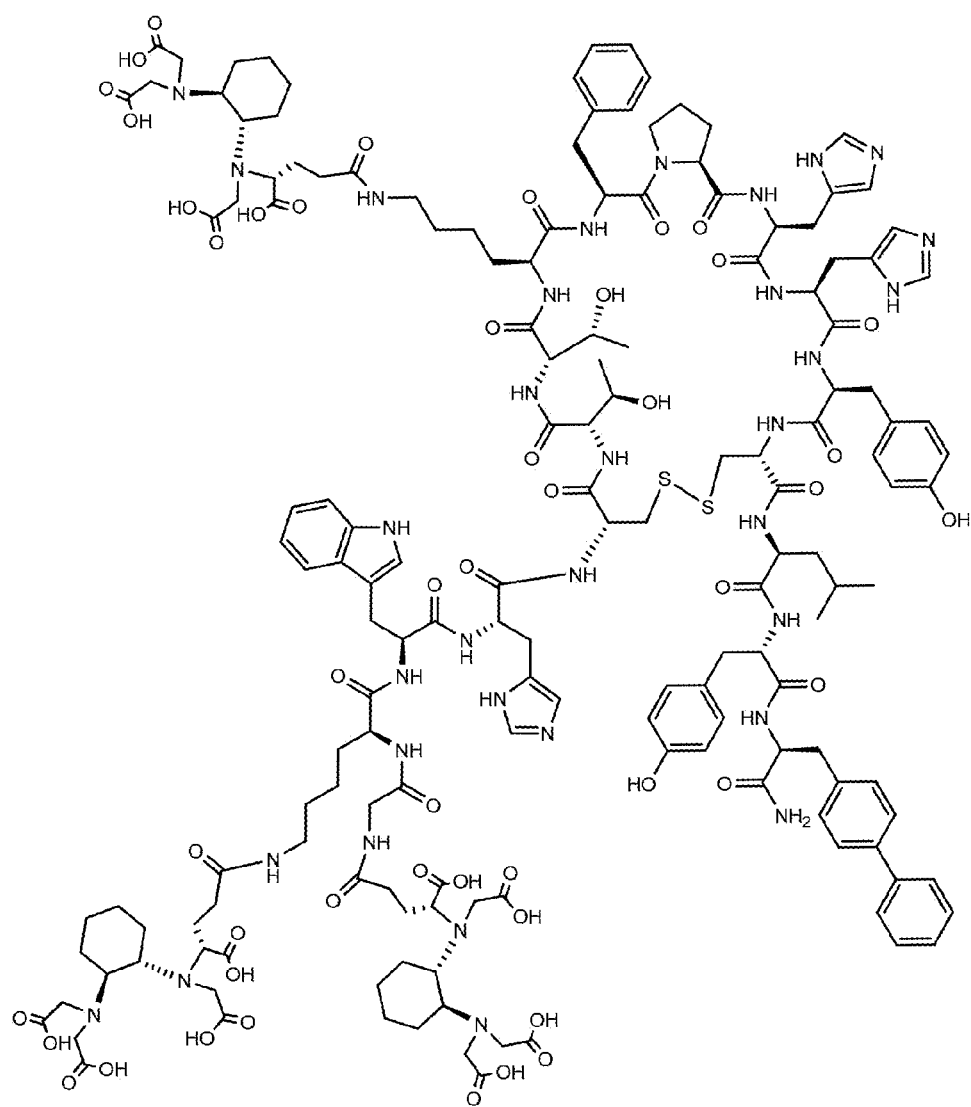

Figure 10. Chemical structure of Compound ID No. 10
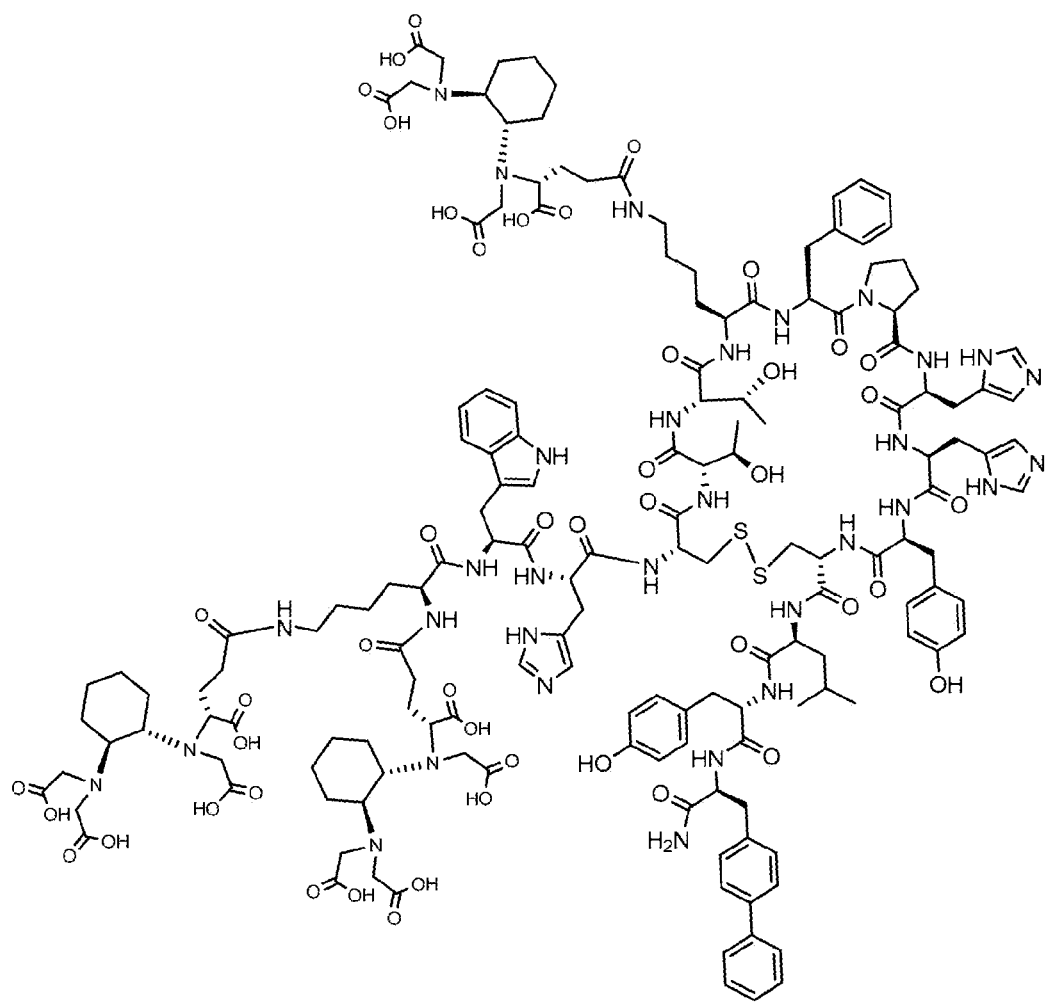

Figure 11. Chemical structure of Compound ID No. 11
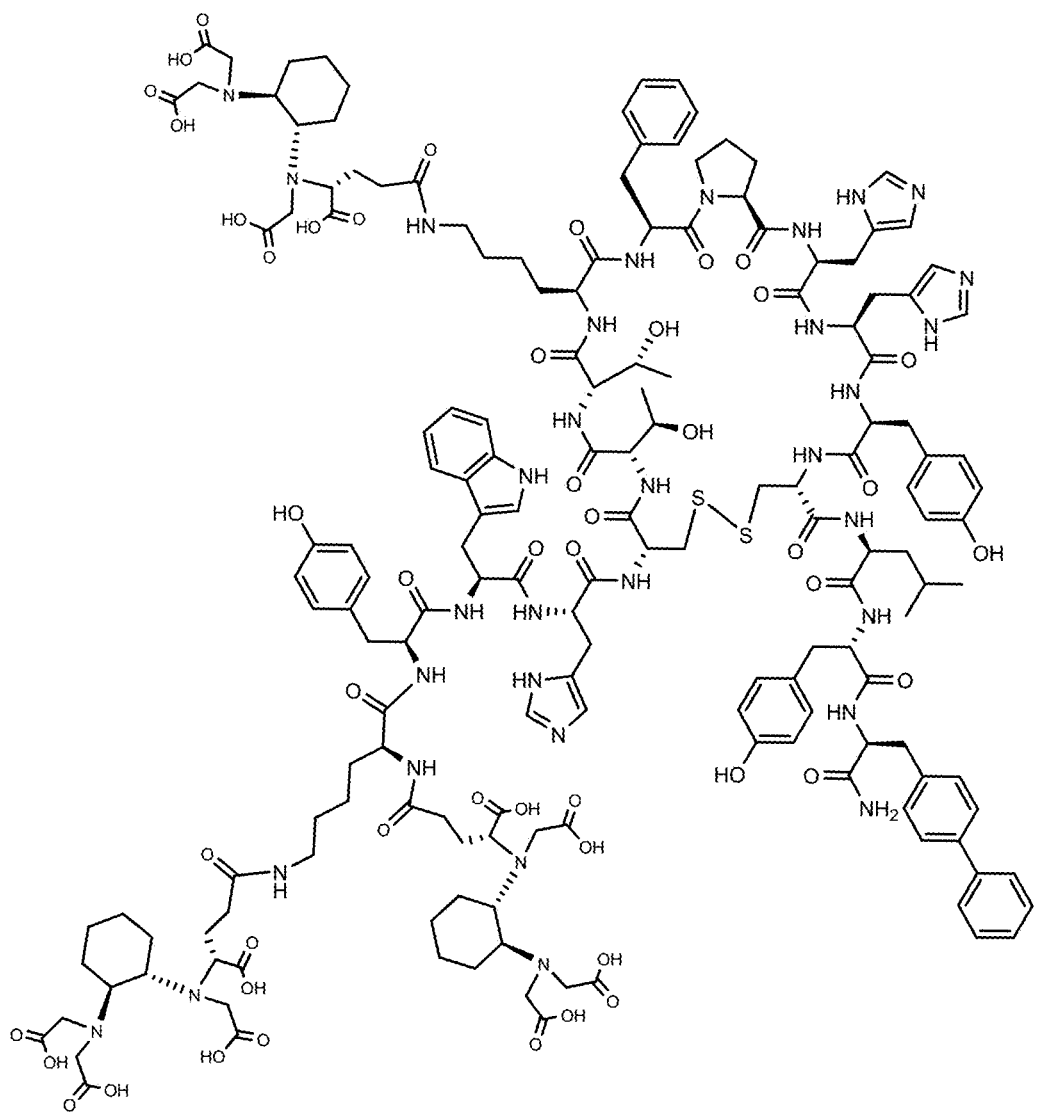

Figure 12. Chemical structure of Compound ID No. 12
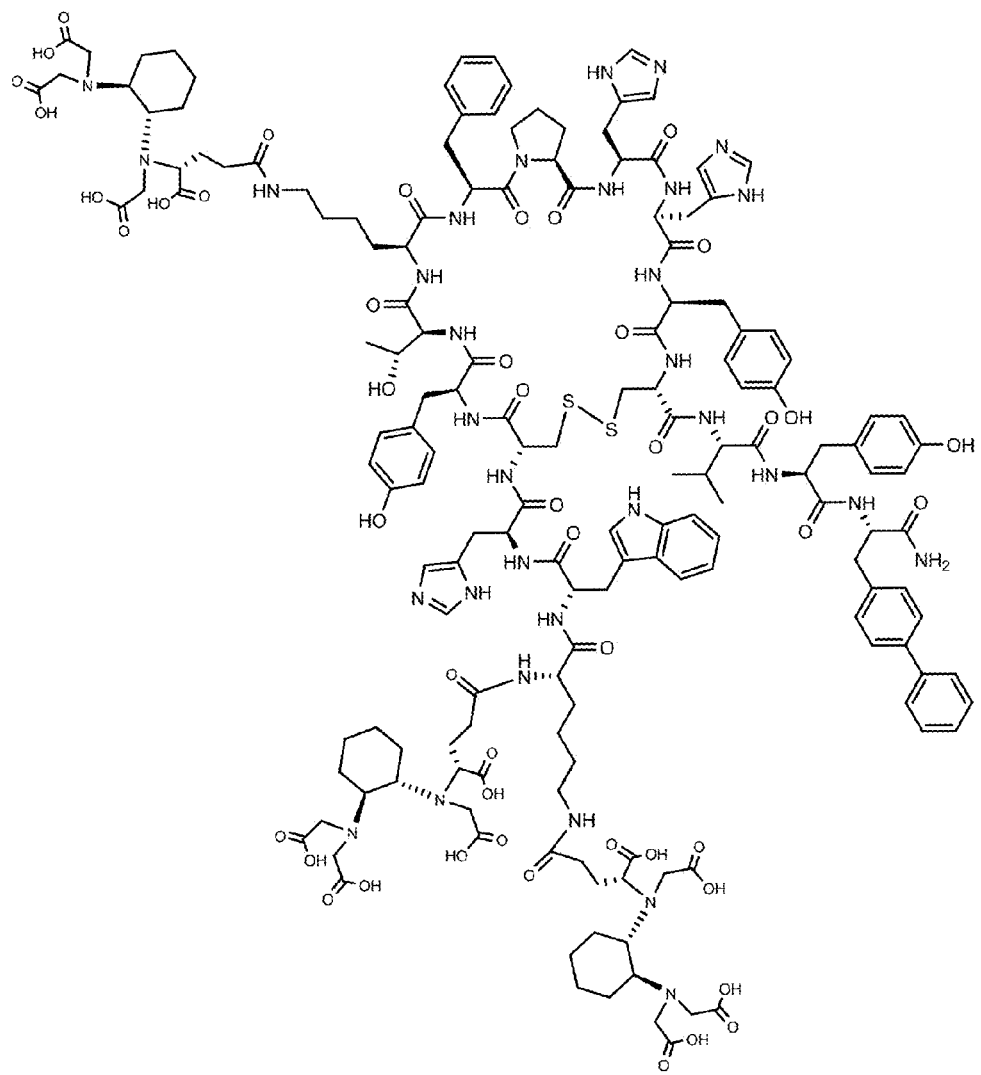

Figure 13. General scheme for preparing the Mn-CDTAGA peptide conjugate compounds
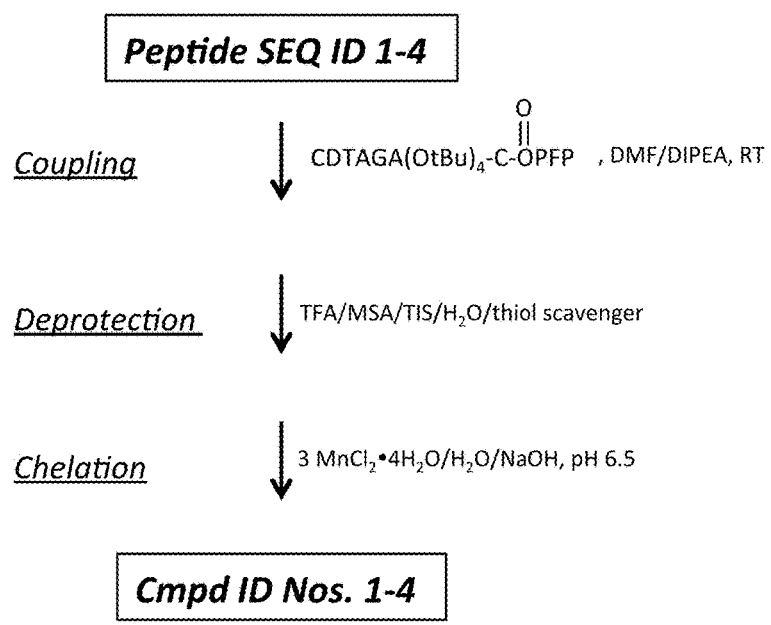

Figure 14. Procedure for synthesizing Compound ID No. 1
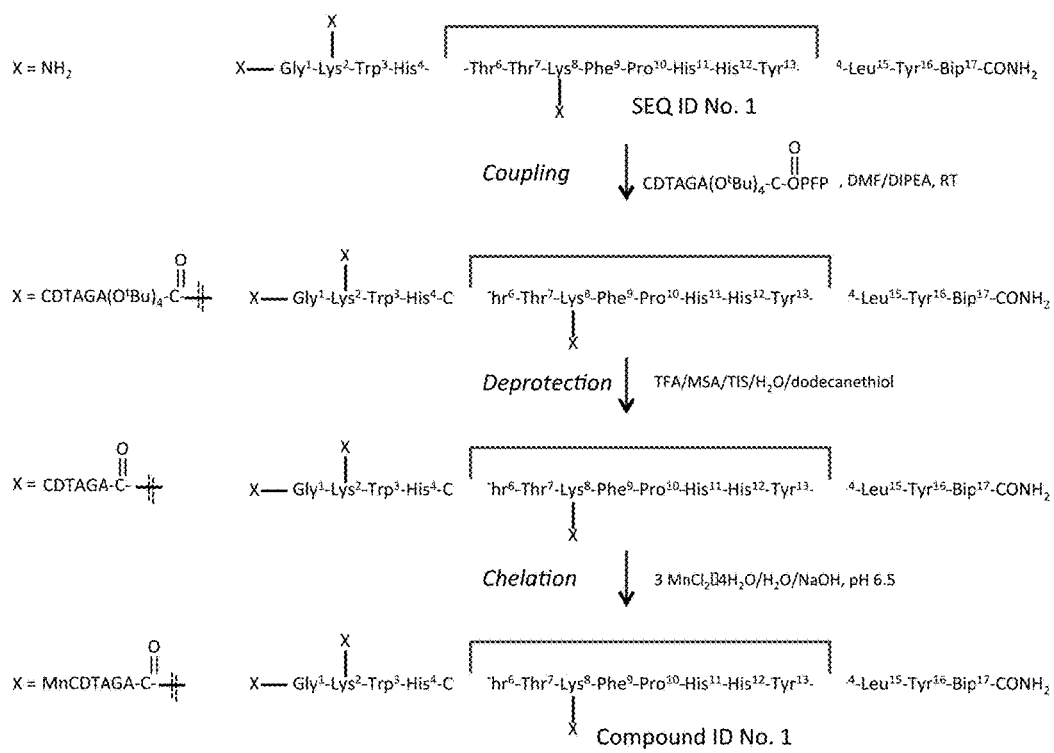

Figure 15. Study design for Compound ID No. 1 assessment of perfusion in a canine model
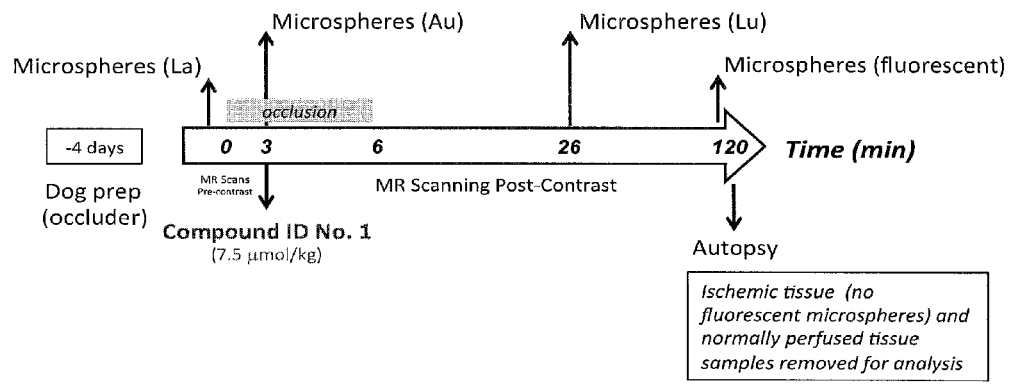

COLLAGEN IMAGING COMPOSITIONS

CROSS-REFERENCE TO RELATED APPLICATIONS

This application claims priority to U.S. Provisional Application Ser. No. 62/186,164, filed on Jun. 29, 2015, the entire contents of which are hereby incorporated by reference.

FEDERALLY SPONSORED RESEARCH

This invention was made with government support under NIH SBIR grants 5R44DK095617-03 (NIDDK); 4R44HL117488-02 (NHLBI), HHSN268201300054C (NHLBI), and HHSN268201400044C (NHLBI). The government has certain rights in the invention.

TECHNICAL FIELD

This disclosure relates to compounds that are capable of binding to, and in some cases, imaging collagen, and more particularly to the use of such compounds and pharmaceutical compositions for organ fibrosis imaging, myocardial imaging and perfusion measurements.

BACKGROUND

Provided herein are improved compounds for binding to and imaging collagen. Also provided herein are pharmaceutical compositions containing the compounds provided herein.

Collagens are a class of extracellular matrix proteins that represent 30% of total body protein and shape the structure of tendons, bones, and connective tissues. Abnormal or excessive accumulation of collagen in organs such as the liver, lungs, kidneys, or breasts, and vasculature can lead to fibrosis of such organs (e.g., myocardial fibrosis, heart failure, nonalcoholic steatohepatitis of the liver (also known as NASH), cirrhosis of the liver, primary biliary cirrhosis), lesions in the vasculature or breasts, collagen-induced arthritis, Muscular dystrophy, scleroderma, Dupuytren's disease, rheumatoid arthritis, and other collagen vascular diseases. It would be useful to have diagnostic agents that could assist in the treatment or diagnosis of such disorders.

Compounds and pharmaceutical compostions for collagen imaging have been previously disclosed in U.S. Pat. No. 8,034,898 and various publications, including Kolodziej, et al., "Peptide optimization and conjugation strategies in the development of molecularly targeted magnetic resonance imaging contrast agents." Methods Mol Biol. 2014; 1088: 185-211, Helm, et al. "Postinfarction myocardial scarring in mice: molecular magnetic resonance (MR) imaging with use of a collagen-targeting contrast agent." Radiology. 2008 June; 247(3): 788-96, and Caravan et al. "Collagen-targeted MRI contrast agent for molecular imaging of fibrosis." Angew Chem Int Ed Engl. 2007; 46(43): 8171-3.

However, improved compounds that exhibit superior binding to collagen of animals used in preclinical studies (especially rodent, canine) along with greater in vivo uptake into collagen tissue and robust imaging enhancement are needed. In addition, because of the association of free gadolinium(III) ions with Nephrogenic Sclerosing Fibrosis (NSF, Thomsen H S. (2009) Nephrogenic systemic fibrosis: history and epidemiology *Radiol Clin North Am.* 47(5): 827-31), there is a need for new derivatives that do not require gadolinium chelates.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the claims.

DESCRIPTION OF DRAWINGS

FIG. 1. shows the chemical structure of Compound ID No. 1

FIG. 2. shows the chemical structure of Compound ID No. 2

FIG. 3. shows the chemical structure of Compound ID No. 3

FIG. 4. shows the chemical structure of Compound ID No. 4

FIG. 5. shows the chemical structure of Compound ID No. 5

FIG. 6. shows the chemical structure of Compound ID No. 6

FIG. 7. shows the chemical structure of Compound ID No. 7

FIG. 8. shows the chemical structure of Compound ID No. 8

FIG. 9. shows the chemical structure of Compound ID No. 9

FIG. 10. shows the chemical structure of Compound ID No. 10

FIG. 11. shows the chemical structure of Compound ID No. 11

FIG. 12. shows the chemical structure of Compound ID No. 12

FIG. 13. is a general scheme for preparing Gd-DOTAGA peptide conjugate compounds.

FIG. 14. shows chemical synthesis steps for preparing Compound ID No. 1.

FIG. 15. is the study design for Compound ID No. 1 assessment of perfusion in a canine model.

DETAILED DESCRIPTION

Definitions

Commonly used chemical abbreviations that are not explicitly defined in this disclosure may be found in The American Chemical Society Style Guide, Second Edition; American Chemical Society, Washington, D.C. (1997), "2001 Guidelines for Authors" *J. Org. Chem.* 66(1), 24A (2001), "A Short Guide to Abbreviations and Their Use in Peptide Science" *J. Peptide. Sci.* 5, 465-471 (1999).

As used herein, the term "peptide" refers to a chain of amino acids that is 16 or 17 amino acids in length. All peptide sequences herein are written from the N to C terminus. Additionally, the peptides described herein contain two or more cysteine residues that can form one or more disulfide bonds under non-reducing conditions. Formation of a disulfide bond can result in the formation of a cyclic peptide.

As used herein, the term "natural" or "naturally occurring" amino acid refers to one of the twenty most common occurring amino acids. Natural amino acids modified to provide a label for detection purposes (e.g., radioactive labels, optical labels, or dyes) are considered to be natural amino acids. Natural L amino acids are referred to by their standard one- or three-letter abbreviations.

For the purposes of this application, "EDTA derivative" refers to a chemical compound comprising a substructure composed of ethylenediamine, wherein the primary amines are each covalently derivatized according to the following formula:

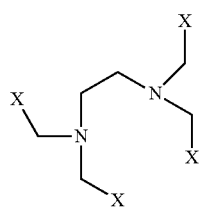

wherein each X is independently a functional group capable of coordinating a metal cation, preferably selected from the group consisting of COOR, C(O)NRR', PO₃RR'⁻, P(R)O₂R', NRR', and OR, wherein R and R' are independently selected from hydrogen, methyl, ethyl, propyl isopropyl, butyl, isobutyl, tert-butyl or other C1 to C6 aliphatic moiety, which can be saturated, unsaturated, cyclic, branched, or straight chain. It is assumed that a person of ordinary skill would understand that, depending on the pH of the medium, certain moieties may be charged or uncharged. Similarly, a person having ordinary skill in the art would understand that the structures can coordinate appropriately charged metal ions. When each X group is the carboxyl moiety (COOH) or carboxylate (COO⁻), then the structure may be referred to as "EDTA". When each X group is the tert-butoxy ($^t$Bu) carboxylate ester (COO$^t$Bu), the structure may be referred to as "EDTE" ("E" for ester). When each X group is the carboxylate (COO⁻) or carboxyl moiety and coordinated to managnese(II) or manganese(III), the structure may be referred to as "MnEDTA" and includes pharmaceutically acceptable salts thereof. It is understood by persons familiar with the art that an exchangeable water molecule (H₂O) may also be coordinated to any such coordinated metal ion. For example, an exchangeable water molecule is typically coordinated to manganese in MnEDTA as well as the nitrogen and oxygen atoms of the EDTA chelating ligand.

For the purposes of this application, "CDTA" refers to a chemical compound comprising a substructure composed of trans-1,2-diaminocyclohexane, wherein the two primary amines are each covalently derivatized according to the following formula:

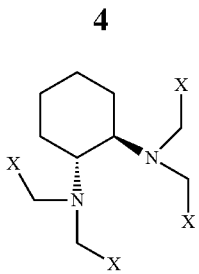

wherein X is defined above. It is assumed that a person of ordinary skill would understand that, depending on the pH of the medium, certain moieties may be charged or uncharged. Similarly, a person having ordinary skill in the art would understand that the structures can coordinate appropriately charged metal ions. When each X group is the carboxylate (COO⁻) and coordinated to manganese(II) or manganese(III), the structure may be referred to as "MnCDTA" and includes pharmaceutically acceptable salts thereof. It is understood by persons familiar with the art that an exchangeable water molecule (H₂O) may also be coordinated to any such coordinated metal ion. For example, an exchangeable water molecule is typically coordinated to manganese in MnCDTA as well as the nitrogen and oxygen atoms of the CDTA chelating ligand.

For the purposes of this application, "1R2R-EDTA" refers to a chemical compound comprising a substructure composed of a 1,2 backbone disubstituted ethylenediamine, wherein the primary amines are each covalently derivatized according to the following formula:

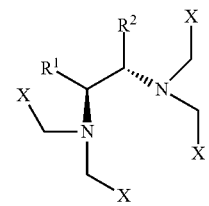

wherein X is defined above. It is assumed that a person of ordinary skill would understand that, depending on the pH of the medium, certain moieties may be charged or uncharged. Similarly, a person having ordinary skill in the art would understand that the structures can coordinate appropriately charged metal ions. It is understood by persons familiar with the art that an exchangeable water molecule (H₂O) may also be coordinated to any such coordinated metal ion.

For the purposes of this application, "CDTAGA derivative" refers to a chemical compound comprising a substructure composed of trans-1,2-diaminocyclohexane, wherein the primary amines are each covalently derivatized according to the following formula,

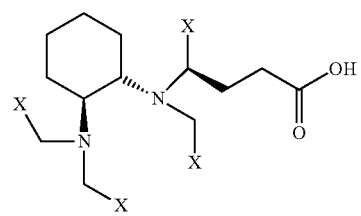

wherein X is defined above and R¹=OH, O-tBu, or NRR'
where R and R' are independently selected from hydrogen, a peptide, methyl, ethyl, propyl isopropyl, butyl, isobutyl, tert-butyl or other C1 to C6 aliphatic moiety, which can be saturated, unsaturated, cyclic, branched, or straight chain. When each X group is the carboxyl moiety (COOH) or carboxylate moiety (COO⁻), then the structure may be referred to as "CDTAGA" and includes pharmaceutically acceptable salts thereof. When each X group is the tert-butoxy ($^t$Bu) carboxylate ester (COO$^t$Bu), the structure may be referred to as "CDTAGA(O$^t$Bu)$_4$". It is assumed that a person of ordinary skill would understand that, depending on the pH of the medium, certain moieties may be charged or uncharged. Similarly, a person having ordinary skill in the art would understand that the structures can coordinate appropriately charged metal ions. When each X group is the carboxylate (COO⁻) and coordinated to manganese(II), the structure may be referred to as "MnCDTAGA" and includes pharmaceutically acceptable salts thereof. It is understood by persons familiar with the art that an exchangeable water molecule ($H_2O$) may also be coordinated to any such coordinated metal ion. For example, an exchangeable water molecule is typically coordinated to the manganese ion in MnCDTAGA as well as the nitrogen and oxygen atoms of the CDTAGA chelating ligand.

The terms "chelating ligand," and "chelating moiety," may be used to refer to any polydentate ligand which is capable of coordinating a metal ion, including EDTA (and EDTE), 1R2R-EDTA, or CDTA as described above, or derivatives thereof, or any other suitable polydentate chelating ligand as is further defined herein, that is either coordinating a metal ion or is capable of doing so, either directly or after removal of protecting groups. The term "chelate" refers to the actual metal-ligand complex, and it is understood that a polydentate ligand can eventually be coordinated to metal ion, which can be a medically useful metal ion.

The terms "target binding" and "binding" for purposes herein refer to non-covalent interactions of a peptide or composition with a target. These non-covalent interactions are independent from one another and may be, inter alia, hydrophobic, hydrophilic, dipole-dipole, pi-stacking, hydrogen bonding, electrostatic associations, or Lewis acid-base interactions. The binding affinity for a target is expressed in terms of the equilibrium dissociation constant "Kd" to the target under a defined set of conditions.

The term "relaxivity" as used herein, refers to the increase in either of the magnetic resonance imaging (MRI) quantities 1/T1 or 1/T2 per millimolar (mM) concentration of paramagnetic ion, contrast agent, or compound, wherein T1 is the longitudinal or spin-lattice, relaxation time, and T2 is the transverse or spin-spin relaxation time of water protons or other imaging or spectroscopic nuclei, including protons found in molecules other than water. Relaxivity is expressed in units of $mM^{-1}s^{-1}$.

As used herein, the term "purified" refers to a peptide or compound that has been separated from either naturally occurring organic molecules with which it normally associates or, for a chemically-synthesized molecule, separated from other organic molecules present in the chemical synthesis. Typically, the polypeptide or compound is considered "purified" when it is at least 70% (e.g., 70%, 80%, 90%, 95%, or 99%), by dry weight, free from any other proteins or organic molecules. The terms "purified" and "isolated" are used interchangeably herein.

As used herein, all references to "Mn" or "manganese" mean the Mn(II) or Mn(III) paramagnetic metal ion.

Collagen Binding Imaging Compounds

Compounds of the invention (e.g., compounds suitable for MR imaging, optical imaging, and nuclear imaging, including PET imaging and SPECT imaging), which can be used for imaging collagen and for detecting pathologies where abnormal or excessive proliferation of collagen is implicated, are described herein. Compounds of the invention include a collagen binding peptide linked to one or more chelating moieties, which in turn may be coordinated to one or more metal ions.

Collagen Binding Peptides

Compounds described herein have an affinity for the extracellular matrix protein collagen, including human and other animal Collagen Type I. Collagens are particularly useful extracellular matrix proteins to target. For example, collagens I and III are the most abundant components of the extracellular matrix of myocardial tissue, representing over 90% of total myocardial collagen and about 5% of dry myocardial weight. The ratio of collagen I to collagen III in the myocardium is approximately 2:1, and their total concentration is approximately 100 μM in the extracellular matrix. Human collagen type I is a trimer of two chains with an [α1(I)]$_2$ [α2(I)] stoichiometry characterized by a repeating G-X-Y sequence motif, where X is most frequently proline and Y is frequently hydroxyproline. In some embodiments, a compound described herein can have an affinity for human, rat, and/or dog collagen type I.

The compounds described herein comprise a collagen binding peptide linked to one or more chelating moieties. Peptides useful for inclusion in the compounds and compositions described herein include natural amino acids and the unnatural amino acid L-4,4'-biphenylalanine (Bip). The peptides can be synthesized according to standard synthesis methods such as those disclosed in, e.g., WO 01/09188 and WO 01/08712. Amino acids with many different protecting groups appropriate for immediate use in the solid phase synthesis of peptides are commercially available.

Peptides can be assayed for affinity to the appropriate extracellular matrix protein by methods as disclosed in WO 01/09188 and WO 01/08712, and as described below. For example, peptides can be screened for binding to an extracellular matrix protein by methods well known in the art, including pull-down assays, equilibrium dialysis, affinity chromatography, and inhibition or displacement of probes bound to the matrix protein. For example, peptides can be evaluated for their ability to bind to collagen, such as dried human, rat or dog collagen type I. In some embodiments acollagen binding peptide can bind human collagen with a dissociation constant of less than 25 μM, less than 10 μM, less than 5 μM, less than 1 μM, or less than 100 nM. In some embodiments the collagen binding peptide can bind rat collagen with a dissociation constant of less than 25 μM, less than 10 μM, less than 5 μM, less than 1 μM, or less than 100 nM. In some embodiments the collagen binding peptide can bind dog collagen with a dissociation constant of less than 25 μM, less than 10 μM, less than 5 μM, less than 1 μM, or less than 100 nM.

A purified peptide of the invention includes one of the following amino acid sequences disclosed herein:
G-K-W-H-C-T-T-K-F-P-H-H-Y-C-L-Y-Bip (SEQ ID No. 1);
K-W-H-C-T-T-K-F-P-H-H-Y-C-L-Y-Bip (SEQ ID No. 2);
K-Y-W-H-C-T-T-K-F-P-H-H-Y-C-L-Y-Bip (SEQ ID No. 3); or K-W-H-C-Y-T-K-F-P-H-H-Y-C-V-Y-Bip (SEQ ID No. 4), wherein Bip is L-4,4'-biphenylalanine.

In a specific embodiment, such a purified peptide includes the amino acid sequence:

```
                                                (SEQ ID No. 1)
            G-K-W-H-C-T-T-K-F-P-H-H-Y-C-L-Y-Bip.
```

In some embodiments, such a purified peptide includes the amino acid sequence:

```
                                                (SEQ ID No. 2)
            K-W-H-C-T-T-K-F-P-H-H-Y-C-L-Y-Bip.
```

In some embodiments, such a purified peptide includes the amino acid sequence:

```
                                                (SEQ ID No. 3)
            K-Y-W-H-C-T-T-K-F-P-H-H-Y-C-L-Y-Bip.
```

In some embodiments, such a purified peptide includes the amino acid sequence:

```
                                                (SEQ ID No. 4)
            K-W-H-C-Y-T-K-F-P-H-H-Y-C-V-Y-Bip.
```

A purified peptide can include any of the amino acid sequences above, also set forth in Table 1, where the peptide has a total length of 16 or 17 amino acids.

ganese trans-1,2-diaminocyclohexanetetraacetate (MnCDTA) are particularly useful. In certain embodiments, acyclic chelating moieties with rigidified backbones such as CDTAGA are preferred. When complexed to manganese(II), the resulting structure may be referred to as "MnCDTAGA" and includes pharmaceutically acceptable salts thereof. The structure of CDTAGA complexed with Mn(II) and having a carboxyl side chain is as follows:

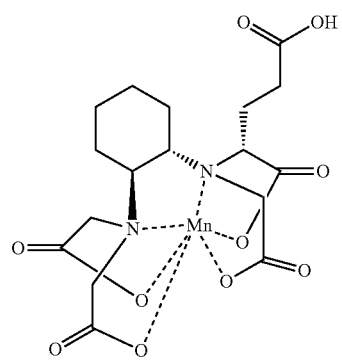

or pharmaceutically acceptable salts thereof. Persons familiar with the art understand that an exchangeable water molecule ($H_2O$) is typically coordinated to manganese as well as the nitrogen and oxygen atoms of the CDTAGA chelating ligand.

TABLE 1

Collagen binding peptides of the invention. Depending on the reducing conditions in the medium, a peptide described herein may be in a linear or cyclic form or a mixture thereof; similarly in a composition comprising a peptide described herein, the peptide may be present as the linear, the cyclic, or a mixture of the cyclic and linear forms.

| SEQ ID | SEQUENCE (AA #) | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| 1 | G | K | W | H | C | T | T | K | F | P | H | H | Y | C | L | Y | Bip |
| 2 | K | W | H | C | T | T | K | F | P | H | H | Y | C | L | Y | Bip | |
| 3 | K | Y | W | H | C | T | T | K | F | P | H | H | Y | C | L | Y | Bip |
| 4 | K | W | H | C | Y | T | K | F | P | H | H | Y | C | V | Y | Bip | |

Chelating Moieties and Chelates

A chelating moiety can be acyclic organic chelating moieties such as EDTA, 1R2R-EDTA, CDTA, or CDTAGA as described above. The term "chelate" refers to a metal-ligand complex.

For magnetic resonance imaging agents, a paramagnetic metal ion such as Gd(III), Fe(III), Mn(II), Mn(III), Cr(III), Cu(II), Dy(III), Ho(III), Er(III), Pr(III), Eu(II), Eu(III), Tb(III), and Tb(IV) can be particularly useful to coordinate to a chelating moiety, and can be complexed to the chelating moieties as previously described. It is understood by persons familiar with the art that an exchangeable water molecule ($H_2O$) may also be coordinated to the paramagnetic metal as part of the chelate. For example, an exchangeable water molecule is typically coordinated to manganese(II) in MnCDTAGA as well as the nitrogen and oxygen atoms of the CDTAGA chelating ligand.

For MRI in fibrosis imaging, metal chelates such as manganese ethylenediaminetetraacetate (MnEDTA) or man- For radionuclide imaging agents, radionuclides $^{60}$Cu, $^{61}$Cu, $^{62}$Cu, $^{64}$Cu, $^{68}$Ga, $^{94}$Tc, $^{86}$Y, $^{89}$Zr, $^{51}$Mn, $^{52}$Mn, $^{44}$Sc, Al, $^{18}$F, $^{90}$Y, $^{99m}$Tc, $^{111}$In, $^{47}$Sc, $^{67}$Ga, $^{51}$Cr, $^{177m}$Sn, $^{67}$Cu, $^{167}$Tm, $^{97}$Ru, $^{188}$Re, $^{177}$Lu, $^{199}$Au, $^{203}$Pb, and $^{141}$Ce are particularly useful, and can be complexed to the chelating moieties described previously.

Metal complexes with useful optical properties also have been described. See, Murru et al., *J. Chem. Soc. Chem. Comm.* 1993, 1116-1118. For optical imaging using chelates, lanthanide chelates such as La(III), Ce(III), Pr(III), Nd(III), Pn(III), Sm(III), Eu(III), Gd(III), Tb(III), Dy(III), Ho(III), Er(III), Tm(III), Yb(III) and Ln(III) are suitable. Eu(III) and Tb(III) are particularly useful.

Metal chelates should not dissociate metal to any significant degree during the imaging agent's passage through the body, including while bound to a target tissue.

Compounds of the invention are synthesized using literature methods described in U.S. Pat. Nos. 6,991,775, 8,034, 898, and elsewhere, such as in Kolodziej et. al. in Andrew E. Nixon (ed.), Therapeutic Peptides: Methods and Protocols, Methods in Molecular Biology, vol. 1088), and as described herein.

The chemical structures of certain compounds of the invention disclosed herein are shown in FIGS. 1-12.

Properties of Compounds

Compounds of the invention, including peptides, peptides conjugated chelates, can be formulated as a pharmaceutical composition in accordance with routine procedures. As used herein, the compounds of the invention can include pharmaceutically acceptable derivatives thereof. "Pharmaceutically acceptable" means that the compound or composition can be administered to an animal without unacceptable adverse effects. A "pharmaceutically acceptable derivative" means any pharmaceutically acceptable salt, ester, salt of an ester, or other derivative of a compound of this invention that, upon administration to a recipient, is capable of providing (directly or indirectly) a compound of this invention or an active metabolite or residue thereof.

Other derivatives are those that increase the bioavailability of the compounds of this invention when such compounds are administered to a animal (e.g., by allowing an orally administered compound to be more readily absorbed into the blood) or which enhance delivery of the parent compound to a biological compartment (e.g., the brain or lymphatic system) thereby increasing the exposure relative to the parent species.

Pharmaceutically acceptable salts of the compounds of this invention include counter ions derived from pharmaceutically acceptable inorganic and organic acids and bases known in the art. Pharmaceutical compositions of the invention can be administered by any route, including both oral and parenteral administration. Parenteral administration includes, but is not limited to, subcutaneous, intravenous, intraarterial, interstitial, intrathecal, and intracavity administration. When administration is intravenous, pharmaceutical compositions may be given as a bolus, as two or more closes separated in time, or as a constant or non-linear flow infusion. Thus, compositions of the invention can be formulated for any route of administration.

Typically, compositions for intravenous administration are solutions in sterile isotonic aqueous buffer. Where necessary, the composition may also include a solubilizing agent, a stabilizing agent, and a local anesthetic such as lidocaine to ease pain at the site of the injection. The composition for intravenous administration may include mannose, dextrose or sucrose. Generally, the ingredients will be supplied either separately, e.g. in a kit, or mixed together in a unit dosage form, for example, as a dry lyophilized powder or water free concentrate. The composition may be stored in a hermetically sealed container such as an ampule or sachette indicating the quantity of active agent in activity units. Where the composition is administered by infusion, it can be dispensed with an 10 infusion bottle containing sterile pharmaceutical grade "water for injection," saline, or other suitable intravenous fluids. Where the composition is to be administered by injection, an ampule of sterile water for injection or saline may be provided so that the ingredients may be mixed prior 15 to administration. Pharmaceutical compositions of this invention comprise the compounds of the present invention and pharmaceutically acceptable salts thereof, with any pharmaceutically acceptable ingredient, excipient, carrier, adjuvant or vehicle.

A compound is preferably administered to the patient in the form of an injectable composition. The method of administering a compound is preferably parenterally, meaning intravenously, intra-arterially, intrathecally, interstitially or intracavitarilly. Pharmaceutical compositions of this invention can be administered to animals including humans in a manner similar to other diagnostic or therapeutic agents. The dosage to be administered, and the mode of administration will depend on a variety of factors including age, weight, sex, condition of the patient and genetic factors, and will ultimately be decided by medical personnel subsequent to experimental determinations of varying dosage followed by imaging as described herein. In general, dosage required for diagnostic sensitivity will range from about 0.001 to 1000 µg/kg, preferably between 0.001 to 25.0 ug/kg of host body mass. The optimal dose will be determined empirically following the disclosure herein.

Compounds of the present invention incorporate the collagen binding peptide sequences described above and physiologically compatible chelating moieties. The compounds thus target extracellular matrix collagen ("the target"), e.g., such as collagen present in the extracellular matrix of the myocardium or liver, and bind to it, allowing imaging of collagen and/or the myocardium or liver.

The extent of binding of a compound to a target can be assessed by a variety of equilibrium binding methods, e.g., ultrafiltration methods; equilibrium dialysis; affinity chromatography; or competitive binding inhibition or displacement of probe compounds. In some cases, peptides can be evaluated for their ability to bind to collagen using assays described herein or as indicated in the cross-referenced application, such as dried human, rat or dog collagen assays. For example, in certain cases, a compound of the invention can bind dried human collagen or dried rat collagen with a dissociation constant of less than 25 µM (e.g., less than 20 µM, less than 10 µM, less than 5 µM, less than 1 µM, or less than 100 nM).

MR compounds can exhibit high relaxivity as a result of binding to collagen, which can lead to better image resolution. The increase in relaxivity upon binding is typically 1.5-fold or more (e.g., at least a 2, 3, 4, 5, 6, 7, 8, 9, or 10 fold increase in relaxivity). Targeted MR compounds having 7-8 fold, 9-10 fold, or even greater than 10 fold increases in relaxivity are particularly useful. Typically, relaxivity is measured using an NMR spectrometer. The preferred relaxivity of an MRI compound at 20 MHz and 37° C. is at least 8 $mM^{-1}s^{-1}$ per paramagnetic metal ion (e.g., at least 10, 15, 20, 25, 30, 35, 40, or 60 $mM^{-1}s^{-1}$ per paramagnetic metal ion). MR compounds having a relaxivity greater than 60 $mM^{-1}s^{-1}$ at 20 MHz and 37° C. are particularly useful.

As described herein, targeted MR compounds can be taken up selectively by areas in the body having higher concentrations of collagen relative to other areas. Selectivity of uptake of targeted agents can be determined by comparing the uptake of the agent by myocardium as compared to the uptake by blood. The selectivity of targeted compounds also can be demonstrated using MRI and observing enhancement of myocardial signal as compared to blood signal.

A compound of the invention may include a variety of physiologically compatible salt forms, including alkali and alkaline earth metal cations, notably sodium. Additional examples inlcude but are not limited to primary, secondary and tertiary amines such as ethanolamine, diethanolamine, morpholine, glucamine, N,N-dimethylglucamine, N-methylglucamine, and amino acids such as lysine, arginine and ornithine.

Use of Compounds

MR compounds prepared according to the disclosure herein may be used in the same manner as conventional MR compounds and are useful for imaging extracellular matrix collagen, including the myocardium and also fibrotic organ tissue which is rich in Collagen Type 1. Typically, a composition comprising the MR compound (an MR composition) is administered to a patient (e.g., an animal, such as a human) and an MR image of the patient is acquired. Generally, the clinician will acquire an image of an area having the extracellular matrix component that is targeted by the agent. For example, the clinician may acquire an image of the heart, a joint, a bone, or an organ (e.g., liver, lung, kidney, heart) if the compound targets collagen or locations of abnormal collagen accumulation in a disease state. The clinician may acquire one or more images at a time before, during, or after administration of the MR compound.

Certain MR techniques and pulse sequences may be preferred in the methods of the present disclosure. Both 2-dimensional and 3-dimensional T1-weighted acquisitions are desirable. For example spin-echo and fast spin echo sequences with short repetition times (TR), or gradient recalled echo sequences with short TR. Inversion recovery sequences may be particularly useful for highlighting T1 changes, as well as the use of an inversion prepulse combined with a T1-weighted sequence. For cardiac imaging methods of cardiac gating, either prospective or retrospective methods, can be applied to freeze cardiac motion. Similarly artifacts from respiratory motion can be reduced using breath-hold methodologies or free-breathing navigator techniques. In some instances it may be desirable to obtain additional contrast and the T1-weighted sequence can be combined with fat suppression, or blood flow suppression, or by using a magnetization transfer prepulse. Similarly, those of skill in the art will recognize other suitable MR-based methods for detecting infarct, e.g., T2 weighted imaging, delayed hyperenhancement imaging following extracellular contrast agent, and myocardial imaging.

In some embodiments, fibrotic pathologies are distinguished from non-fibrotic pathologies using a method comprising (a) administering to the animal an effective amount of an MR composition comprising Compound ID No. 1, 2, 3 or 4; (b) acquiring a T1-weighted image of a tissue of said animal at from about 1 minute to about 10 minutes after administration of the MR composition; (c) acquiring a second T1-weighted image of the tissue of said animal at a time from about 10 minutes to about 2 hours after administration of the MR composition; and evaluating differences between the images acquired in steps (b) and (c), wherein a non-fibrotic tissue exhibits greater loss in enhancement from the image collected in step (b) to that in step (c) as compared to a fibrotic pathology.

In another embodiment, a method of distinguishing fibrotic from non-fibrotic pathologies in an animal comprises (a) administering to the animal an effective amount of an MR composition, the MR composition comprising Compound ID No. 1, 2, 3 or 4; (b) measuring R1 (1/T1) of a tissue of said animal at from about 1 minute to about 60 minutes after administration of the composition; and (c) comparing R1 of the tissue to a reference value for that tissue whereby the tissue is fibrotic if the R1 value is greater than the reference value.

In a further embodiment, a method of distinguishing fibrotic from non-fibrotic pathologies in an animal comprises: (a) measuring R1 (1/T1) of a tissue of said animal; (b) administering to the animal an effective amount of an MR composition, the MR composition comprising Compound ID No. 1, 2, 3 or 4; (c) measuring R1 (1/T1) of a tissue of said animal at from about 1 minute to about 60 minutes after administration of the composition; and (d) comparing the difference in R1 of the tissue before and after administration of an MR composition, the MR composition comprising Compound ID No. 1, 2, 3 or 4 (delta-R1) to a reference value for that tissue whereby the tissue is fibrotic if the delta-R1 value is greater than the reference value.

In some embodiments, a contrast-enhancing imaging sequence that preferentially increases a contrast ratio of a magnetic resonance signal of tissue, such as the myocardium, having a MR compound bound thereto relative to the magnetic resonance signal of background or flowing blood is used. These techniques include, but are not limited to, black blood angiography sequences that seek to make blood dark, such as fast spin echo sequences; flow-spoiled gradient echo sequences; and out-of-volume suppression techniques to suppress in-flowing blood. These methods also include flow independent techniques that enhance the difference in contrast due to the T1 difference between contrast-enhanced myocardium and blood and tissue, such as inversion-recovery prepared or saturation-recovery prepared sequences that will increase the contrast between the myocadium and background tissues. Methods of preparation for T2 techniques may also prove useful. Finally, preparations for magnetization transfer techniques may also improve contrast with MR compounds.

Methods may be used that involve the acquisition and/or comparison of contrast-enhanced and non-contrast images and/or the use of one or more additional MR appropriate compounds, which may be referred to herein as MR compounds. The additional MR compounds may also exhibit affinity for an extracellular matrix component of the myocardium, as described herein. For example, a series of images may be obtained with an MR compound that binds to collagen, while another series of images may be obtained with an MR compound that binds to elastin. Alternatively, an additional MR compound may be used that is nonspecific or that may exhibit an affinity for fibrin or HSA. For example, methods as set forth in U.S. patent application Ser. No. 09/778,585, entitled MAGNETIC RESONANCE ANGIOGRAPHY DATA, filed Feb. 7, 2001 and U.S. patent application Ser. No. 10/209,416, entitled SYSTEMS AND METHODS FOR TARGETED MAGNETIC RESONANCE IMAGING OF THE VASCULAR SYSTEM, filed Jul. 30, 2002 may be used. Similarly, fibrin targeted agents are described in U.S. patent application Ser. No. 10/209,183, entitled PEPTIDE-BASED MULTIMERIC TARGETED CONTRAST AGENTS, filed Jul. 30, 2002. Compounds for binding HSA are described in WO 96/23526.

In addition, MR compounds are useful for monitoring and measuring myocardial perfusion. Certain methods include the step of obtaining an MR image of the myocardial tissue of an animal while the animal is in a pre-hyperemic state. As used herein, the term "pre-hyperemic state" refers to a resting physiologic state of the animal. In some methods, peak hyperemia can be induced in the animal, either before or after the step of obtaining a pre-hyperemic MR image. As used herein, the term "peak hyperemia" means the point approaching maximum increased blood supply to an organ or blood vessel for physiologic reasons. Peak hyperemia can be exercise-induced or pharmacologically-induced. Exercise-induced peak hyperemia can be achieved through what is commonly known as a "stress test," and has several clinically relevant endpoints, including excessive fatigue, dyspnea, moderate to severe angina, hypotension, diagnostic ST depression, or significant arrhythmia. If exercise is used to induce peak hyperemia, the animal can exercise for at least one additional minute before the administration of a compound, as described below. The cardiac effect of exercise-induced peak hyperemia can also be simulated pharmacologically (e.g., by the intravenous administration of a coronary vasodilator, such as Dipyridamole (Persantine™)) or adenosine.

After or during the induction of peak hyperemia, an effective amount of an MR composition comprising Compound ID No. 1, 2, 3 or 4 can be administered to the animal. An MR image of the animal's myocardial tissue after the induction of peak hyperemia can then be acquired. Generally, the acquisition of the image begins at a time frame at least 2 times greater than that required for a first pass distribution of Compound ID No. 1, 2, 3 or 4. In humans, with venous injection of an MR compound, the bolus typically passes through the right heart after approximately 12 sec., and through the left heart after about another 12 sec. Thus, from time of injection to the first pass of the MR compound through the entire heart, approximately 24-30 seconds have passed usually. The second pass of the MR compound usually is seen approximately 45 sec. later. In some embodiments, the MR image of the myocardial tissue of the animal after the induction of peak hyperemia may begin at a time frame at least 5, 10, or 30 times greater than that required for a first pass distribution of the MR compound. Typically, the acquisition of the MR image of the myocardial tissue after the induction of peak hyperemia begins in a time period from about 5 to about 60 minutes after the induction of peak hyperemia. For example, in some embodiments, peak hyperemia is induced in the patient outside of an MR scanner, the MR composition comprising Compound ID No. 1, 2, 3 or 4 is injected at or after peak hyperemia, and the patient is put inside the MR scanner to acquire the MR image of the myocardium after peak hyperemia.

In certain embodiments, the MR images of the myocardium, whether at peak or pre-hyperemia, are T1-weighted images. In some embodiments, T2-weighted images of the myocardium in a pre-hyperemic state are obtained. A T2 weighted image of the myocardium at rest (pre-hyperemic) would give an enhancement of infarcted tissue.

In certain cases, the MR image of the myocardial tissue of the animal in the pre-hyperemic state, if obtained, are compared with the MR image of the myocardial tissue after the induction of peak hyperemia in order to evaluate myocardial perfusion. Zones of abnormal, or low, perfusion will be hypointense (less intense) compared to normal myocardium in the peak hyperemia image.

Certain methods employ a second MR compound. In these methods, peak hyperemia can be induced in an animal and an effective amount of a first MR composition, an MR composition comprising Compound ID No. 1, 2, 3 or 4, is administered. An MR image of the animal's myocardial tissue after the induction of peak hyperemia is acquired, as described previously. An effective amount of a second MR composition can then be administered. In some embodiments, the first and second MR compositions are administered together. The second MR composition may comprise any MR compound including ECF agents or the compounds described herein. Suitable examples of Gd(III)-complexed MR compounds include MnCDTA, Gd(III)-DTPA, Gd(III)-DOTA; Gd(III)-DOTAGA; Gd(III)-HP-DO3A, Gd(III)-DTPA-BMA, Gd(III)-DTPA-BMSA, Gd(III)-BOPTA, Gd(III)-EOB-DTPA, Gd(III)-MS-325, Gd(III)-Gadomer-17, or the Gd(III)-complex of the first MR compound administered in the method. Other examples of useful compounds are described in WO 96/23526. The administration of the second MR composition can occur after a time frame sufficient to return the animal to a pre-hyperemic state. For example, the animal may immediately return to a pre-hyperemic state, or the administration of the second compound can occur on a time frame typically ranging from 15 min. to approximately 4 hours after the induction of peak hyperemia. An MR image of the myocardial tissue of the animal in the pre-hyperemic state is then acquired. As one of skill in the art can recognize, the order of the above-referenced steps can be altered, e.g., the administration of the "second" MR composition and acquisition of the pre-hyperemic image can be performed first, while the administration of the "first" MR composition and peak hyperemic scan could be acquired second.

An MR image of the myocardial tissue of the animal in the pre-hyperemic state can be compared with the MR image of the myocardial tissue after the induction of peak hyperemia. Zones of abnormal, or low, perfusion will be hypointense compared to normal myocardium in the peak hyperemia image. Both ischemic and infarct zones appear as hypointense in the peak hyperemia image. In the pre-hyperemic image acquired with the second compound, however, the ischemic zones appear with normal to hyperintensity, while infarct zones initially appear as hypointense (e.g., after a short time period after injection of the second compound) and then as hyperintense after a longer delay after injection. A comparison of the two images thus allows the characterization of abnormal, or low, perfusion as either ischemia or infarct.

In other methods of evaluating myocardial perfusion, peak hyperemia is induced and an MR composition is administered. An MR image of the animal's myocardial tissue after the induction of peak hyperemia is acquired. The animal is allowed to return to a pre-hyperemic state, and the myocardial tissue is imaged again. The two images can then be compared and examined for zones of ischemia and/or infarct.

Administering an MR composition as described herein (e.g., composition comprising a collagen targeted compound such as one of Compound No. 1, 2, 3, or 4) at peak hyperemia should yield an MR image where healthy tissue is bright, while inducibly ischemic and infarcted tissue is dark, for T1 weighted scans. If there is a dark (hypointense region), one can distinguish whether it is viable tissue (inducible ischemia) or if it is an infarct by comparing the image to an image of the myocardium obtained using one or more of several other methods. For example, one method would be to acquire a T2-weighted scan of the myocardium at rest (e.g., either before or after the induction of peak hyperemia). Infarct appears bright relative to normal compound as described herein (e.g., a collagen targeted MR compound) at rest (pre-hyperemia) and to obtain a pre-hyperemic MR scan of the myocardium, as described previously above; this administration could be performed either before or after the peak hyperemia MR scan. In such a pre-hyperemic scan, normal and inducibly ischemic tissue would enhance, but infarct would not (analogously to nuclear medicine protocols). A third approach would be to administer a composition comprising an extracellular fluid MR compound (ECF), e.g., MnCDTA or GdDOTA, or others as known to those having ordinary skill in the art, at pre-hyperemia, and to obtain an MR image of the myocardium from about 2 to about 60 (e.g., 2 to 20, 2 to 10, 5 to 10, 5 to 20, 10 to 30, 5 to 40, or 8 to 50) minutes after administration of the ECF, e.g., a delayed enhancement image. In this case the infarct would enhance, but the ischemic area would not. Finally, a fourth approach would be to administer a composition comprising an ECF agent at pre-hyperemia and to perform a first pass (MRFP) dynamic perfusion exam to determine if hypointense areas as seen in the targeted MR agent hyperemia scans enhance as quickly and intensely as normal myocardium, which would indicate inducible ischemia.

In one embodiment, method of magnetic resonance (MR) imaging for evaluating myocardial perfusion in an animal comprises (a) inducing peak hyperemia in an animal; (b) administering to the animal an effective amount of an MR composition, the MR composition comprising Compound ID No. 1, 2, 3 or 4; (c) acquiring an MR image of the animal's myocardial tissue after the induction of peak hyperemia in the animal, the acquisition of the MR image beginning at a time frame at least 2 times greater than that required for a first pass distribution of the MR compound; (d) acquiring a second MR image of the animal's myocardial tissue after the induction of peak hyperemia in the animal, the acquisition of the MR image beginning at a time frame at least 4 times greater than that required for a first pass distribution of the MR compound; and (e) evaluating said images of the animal's myocardial tissue to evaluate myocardial perfusion. In some embodiments the method may further comprise acquiring an MR image of the myocardial tissue of the animal in a pre-hyperemic state either before the induction of peak hyperemia in the animal or after a sufficient period of time after the induction of peak hyperemia in the animal to allow the animal to return to a pre-hyperemic state.

In another embodiment, a method of magnetic (MR) imaging for evaluating myocardial perfusion in an animal comprises: (a) inducing peak hyperemia in an animal; (b) administering to the animal an effective amount of an MR composition, the MR composition comprising Compound ID No. 1, 2, 3 or 4; (c) acquiring an MR image of the animal's myocardial tissue after the induction of peak hyperemia in the animal, the acquisition of the MR image beginning at a time frame at least 2 times greater than that required for a first pass distribution of the MR compound; and (d) evaluating said images of the animal's myocardial tissue to evaluate myocardial perfusion. In some embodiments the method may further comprise acquiring an MR image of the myocardial tissue of the animal in a pre-hyperemic state either before the induction of peak hyperemia in the animal or after a sufficient period of time after the induction of peak hyperemia in the animal to allow the animal to return to a pre-hyperemic state.

The compounds of the present disclosure may function to distinguish benign from malignant breast lesions or tumors. Benign lesions such as fibroadenomas and fibrocystic tissue contain significant concentrations of type I collagen. Carcinomas are also collagen rich compared to normal breast tissue that may serve to provide a signature for staging cancer.

In certain embodiments, a compound of the present disclosure (e.g., Compound ID Nos. 1, 2, 3 or 4) may be used. In some embodiments, a T1-weighted imaging is performed after injection of the compound, and a dynamic phase shows all lesions enhanced. The compound is retained in the collagen-rich benign lesions, but washes out of the carcinoma. An image is then acquired at a later time point (e.g., 10 minutes or more post injection) and the benign lesion remains enhanced whereas the carcinoma is not enhanced at this late time point.

In another embodiment, the dynamic contrast-enhanced magnetic resonance imaging (DCE-MRI) approach is used with Compound ID Nos. 1, 2, 3 or 4. Collagen binding alters the signal intensity vs time curve, especially at later time points where the wash-out from the benign lesion is much slower than from the carcinoma.

It is also contemplated that the compounds set forth in this disclosure may be useful in the following applications:

1. Atherosclerosis, High Risk/Vulnerable Plaque.

It has become established that certain atherosclerotic lesions are at risk for rupture, thereby creating a thrombogenic surface. Plaque rupture leads to thrombosis which can result in myocardial infarction or stroke. The precursor lesion of plaque rupture has been defined (Virmani et al, J Intery Cardiol. 2002, 15:439-46) as "thin-cap fibroatheroma" (TCFA). Morphologically, TCFAs have a necrotic core with an overlying thin fibrous cap (<65 mm) consisting of collagen type I, which is infiltrated by macrophages. These lesions are most frequent in the coronary tree of patients dying with acute myocardial infarction. In TCFAs, necrotic core length is approximately 2-17 mm (mean 8 mm) and the underlying cross-sectional luminal narrowing in over 75% of cases is <75% (<50% diameter stenosis). The area of the necrotic core in at least 75% of cases is <3 mm$^2$. Clinical studies of TCFAs are limited as angiography and intravascular ultrasound (IVUS) catheters cannot precisely identify these lesions. Identification of these precursor lesions of plaque rupture is therefore a great unmet medical need.

Stable lesions, on the other hand, have a thick fibrous (collagenous) cap. The ability to identify and distinguish atherosclerotic plaques based on cap thickness would be of great value. A collagen type I targeted imaging agent such as those described in this application, would bind to the fibrous cap in a collagen-dependent manner. Stable plaques would be seen by T1-weighted MRI as hyperenhanced regions in the lumen and vessel wall. Unstable or at risk plaques (the TCFA) would be seen as a thin hyperenhanced complex zone appearing along the vessel wall.

2. Myocardial Infarct Imaging and Myocardial Viability.

It has been demonstrated that delayed enhancement of infarcted myocardium with GdDTPA enhanced Mill is useful for detecting both transmural and subendocardial infarcts (e.g. Wagner et al. Lancet 2003, 361:374-9). Myocardial infarcts (MI) are typically classified by their EKG response and are grouped into Q-wave MI and non-Q-wave MI. Non-Q-wave infarcts are typically smaller infarcts, however they are associated with a morbidity and mortality associated with larger infarcts. Wagner et al. showed that delayed contrast enhancement Mill was much better at detecting subendocardial infarcts than single photon emission computed tomography (SPECT). Improving the detection of infarct to identify smaller MI would result in a change in treatment for these patients whose MI would otherwise have been missed and would likely improve prognosis. MI results in cardiac remodeling and an increased collagen content. A specific collagen targeted contrast agent would be able to better delineate infarcted regions and improve specificity for infarct.

3. Myocardial Fibrosis—Diagnosis, and Monitoring Response to Therapy.

The extent of myocardial fibrosis is strongly associated with adverse myocardial remodeling, heart failure, life threatening arrhythmias, and early mortality in patients with ischemic and non-ischemic cardiac disorders. A method that allows the identification of early pathological fibrosis and subsequent monitoring of the progression of fibrosis would be useful in identifying at-risk individuals with poor prognosis as well as provide a means for testing the efficacy of new therapies aimed at halting progression of fibrosis. Healthy myocardium is composed of myocardial tissue (80%) with the remaining 20% including the extracellular matrix, is composed of collagen scaffolding.

A hallmark of abnormal cardiac pathology is the expansion of the extracellular volume (ECV) through the development of fibrosis, with increased deposition of type I collagen by cardiac fibroblasts. This occurs in a wide array of cardiac disease including ischemic and non-ischemic cardiomyopathies, which may deposit in different patterns throughout the myocardium. These may either be focal, as found in healed myocardial infarction, or globally distributed throughout the myocardium. As the disease progresses, pathologic fibrosis may be concentrated regionally in addition to being present globally.

Therefore, a specific collagen targeted contrast agent would be ideal for imaging myocardial fibrosis in these patients.

4. Renal Fibrosis—Diagnosis, and Monitoring Response to Therapy.

Renal fibrosis is a final common process of many chronic renal diseases. It is characterized by overdeposition of the extracellular matrix, notabl collagen, which eventually leads to the end-stage renal disease (ESRD). Several renal disorders such as diabetic nephropathy, chronic glomerulonephritis, tubulointerstitial fibrosis and hypertensive nephrosclerosis can result into ESRD. Early detection of renal fibrosis would be valuable in order to start treatments earlier and improve the likelihood of reversing the disease. Moreover an imaging agent that allows monitoring of fibrosis would be valuable in assessing response to therapy.

5. Pulmonary Fibrosis—Diagnosis, and Monitoring Response to Therapy.

Pulmonary fibrosis is a pathology whereby the lung tissue becomes scarred with deposits of fibrotic (collagen) tissue. As fibrosis increases there is a decrease in the lung's ability to transfer oxygen to the blood resulting in considerable morbidity and a high likelihood of mortality. There are many causes of pulmonary fibrosis: environmental pollutants/toxins such as cigarette smoke, asbestos; diseases such as scleroderma, sarcoidosis, lupus, rheumatoid arthritis; side effects of radiation treatment or chemotherapy (e.g. bleomycin treatment) for cancer. Early detection and accurate characterization of pulmonary fibrosis can improve patient outcomes. Moreover, as new antifibrotic therapies become available there is a need for means of non-invasively monitoring pulmonary fibrosis and the patient's response to therapy.

6. Liver Fibrosis—Diagnosis, and Monitoring Response to Therapy.

Liver fibrosis is a common result of many diseases which attack the liver: hepatitis B and C; non-alcoholic steatohepatitis (NASH); cirrhosis; primary biliary cirrhosis (PBC); primary sclerosing cholangitis (PSC); and occurs in a fraction of patients with fatty liver. Fibrosis in the liver can be diagnosed but only at an advanced stage with current non-invasive procedures. Biopsy can detect fibrosis at an earlier stage but liver biopsy is not well suited to screening/monitoring disease because of its cost, associated morbidity and known lack of accuracy because of sampling variation, Rockey D C, Bissell D M. "Noninvasive measures of liver fibrosis" Hepatology. 2006 43:S113-20. Early detection and accurate characterization of liver fibrosis can improve patient outcomes. For patients with NASH, diet changes can reverse the disease if caught early enough. Moreover, as new antifibrotic therapies become available there is a need for means of non-invasively monitoring pulmonary fibrosis and the patient's response to therapy.

7. Scleroderma—Diagnosis of Organ Fibrosis and Monitoring Response to Therapy.

Sceloderma is a rare chronic autoimmune disease with an annual incidence of about 20 cases per million in the United States. The disease is characterized by diffuse skin fibrosis, but systemic sleroderma can also affect internal organs. Currently there are no diagnostic tests to enably physians to determine whether or not fibrosis is spreading to internal organs. Early detection of lung, cardiac or renal fibrosis would enable sleroderma patients to be prioritized for new anti-fibrotic therapies.

Pharmaceutical Compositions

Pharmaceutical compositions can include any of the compounds described previously, and can be formulated as a pharmaceutical composition in accordance with routine procedures. As used herein, pharmaceutical compositions can include pharmaceutically acceptable salts or derivatives thereof "Pharmaceutically acceptable" means that the agent can be administered to an animal without unacceptable adverse effects. A "pharmaceutically acceptable salt or derivative" means any pharmaceutically acceptable salt, ester, salt of an ester, or other derivative of composition that, upon administration to a recipient, is capable of providing (directly or indirectly) a composition of the present disclosure or an active metabolite or residue thereof. Other derivatives are those that increase the bioavailability when administered to a animal (e.g., by allowing an orally administered compound to be more readily absorbed into the blood) or which enhance delivery of the parent compound to a biological compartment (e.g., the brain or lymphatic system) thereby increasing the exposure relative to the parent species. Pharmaceutically acceptable salts of the compounds or compositions of this disclosure include counter ions derived from pharmaceutically acceptable inorganic and organic acids and bases known in the art, e.g., sodium, calcium, N-methylglutamine, lithium, magnesium, potassium, etc.

Pharmaceutical compositions can be administered by any route, including oral, intranasal, inhalation, or parenteral administration. Parenteral administration includes, but is not limited to, subcutaneous, intravenous, intraarterial, interstitial, intrathecal, and intracavity administration. When administration is intravenous, pharmaceutical compositions may be given as a bolus, as two or more doses separated in time, or as a constant or non-linear flow infusion. Thus, compositions can be formulated for any route of administration.

Typically, compositions for intravenous administration are solutions in sterile isotonic aqueous buffer. Where necessary, the composition may also include a solubilizing agent, a stabilizing agent, and a local anesthetic such as lidocaine to ease pain at the site of the injection. Generally, the ingredients will be supplied either separately, e.g. in a kit, or mixed together in a unit dosage form, for example, as a dry lyophilized powder or water free concentrate. The composition may be stored in a hermetically sealed container such as an ampule or sachette indicating the quantity of active agent in activity units. Where the composition is administered by infusion, it can be dispensed with an infusion bottle containing sterile pharmaceutical grade "water for injection," saline, or other suitable intravenous fluids. Where the composition is to be administered by injection, an ampule of sterile water for injection or saline may be provided so that the ingredients may be mixed prior to administration. Pharmaceutical compositions comprise the compounds of the present disclosure and pharmaceutically acceptable salts thereof, with any pharmaceutically acceptable ingredient, excipient, carrier, adjuvant or vehicle.

A pharmaceutical composition is preferably administered to the patient in the form of an injectable composition. The method of administering a compound is preferably parenterally, meaning intravenously, intra-arterially, intrathecally, interstitially or intracavitarilly. Pharmaceutical compositions can be administered to animals including humans in a manner similar to other diagnostic or therapeutic agents. The dosage to be administered, and the mode of administration will depend on a variety of factors including age, weight, sex, condition of the patient and genetic factors, and will ultimately be decided by medical personnel subsequent to experimental determinations of varying dosage followed by imaging as described herein. In general, dosage required for diagnostic sensitivity will range from about 0.1 to 100 mg/kg, preferably between 1 to 40 mg/kg of host body mass. The optimal dose will be determined empirically following the disclosure herein.

EXAMPLES

Synthesis of Collagen Binding Peptides

Synthetic collagen binding peptides with amidated C-terminii (Table 1, Sequence ID Nos. 1-4) are synthesized using standard solid phase peptide synthesis methods as described herein.

Peptides are synthesized on an automated peptide synthesizer "Liberty Blue" (CEM Inc.) using 1 to 12 batch reactors loaded with 0.1 mmol of commercially available Rink amide resin (~0.38 mmol/g). A single coupling cycle is used for each amino acid and a 5-fold excess of amino acids is used per coupling to synthesize the peptide on the resin. Standard Fmoc chemistry is used to elongate the peptide on the resin. The Fmoc is removed with a solution of 20% piperidine and 0.1M HOBt in DMF. Each amino acid is dissolved in DMF to give a 0.2 M solution and is coupled to the peptide using a 0.5 M solution of diisopropylcarbodiimide in DMF, and 1.0M Oxyma (or HOBt) After each deprotection or coupling step the resin is washed three times with DMF. The completed peptide/resin is washed with 1:1 DCM:CH$_2$Cl$_2$ and transferred back to the falcon tube, in ca. 20 mL of 1:1 DCM:CH$_2$Cl$_2$ mixture.

After the synthesis of the peptide on the resin is complete, the peptide is filtered and subsequently cleaved from the resin using the following cleavage cocktail: TFA/TIS/H$_2$O 95:2.5:2.5 (10 mL per 100 μmoles of peptide). The solution of fully deprotected peptide is precipitated with diethyl ether (40 mL). The peptide solid is isolated after centrifugation and decantation and then re-dissolved in a 1:1 mixture of DMSO/10 mM NH$_4$OAc (ca. 40 mL). The cyclization is monitored by LC-MS (24 h). The cyclic peptide is purified by reverse phase preparative HPLC on a C-5 column using a gradient of 5% mobile phase A (0.1% TFA in water) to 60% mobile phase B (0.1% TFA in acetonitrile) over 23 minutes. The fractions of pure peptide are pooled and lyophilized to give the final peptide moiety.

Synthesis of Collagen Binding Compounds

Procedure for Preparing the MnCDTAGA Peptide Conjugate Compounds (FIG. 13, Compound ID Nos. 1-4)

Chelate Coupling:

t-butyl protected CDTAGA-pentafluorophenylester is prepared by first reacting the mesylate derivative of 2-(S)-2-Hydroxypentanedioic acid, 1-tert-butyl-5-benzyl ester (Levy, Organic Process Research & Development 2009, 13, 535-542) with excess trans-1,2-cyclohexyldiamine, isolating the monoalkylated derivative, and then alkylating the remaining 3 primary amines with bromo-tbutyl acetate. The cyclized peptide (0.05 mmol) containing N primary amines is dissolved in DMF (15 ml). t-butyl protected CDTAGA-pentafluorophenylester (1.2×N primary amines×0.05 mmol) is added and the pH (measured on wet pH stick) of the reaction mixture adjusted to 6.5-7.5 with di-isopropylethylamine (DIEA). The reaction is stirred overnight at room temperature and upon completion of the reaction, verified by LC/MS is then triturated with brine and washed with water to give a solid. The solid is filtered and dried under vacuum overnight. Purity and identity are confirmed by LC-MS and the product is used without further purification.

Deprotection:

The crude product, protected CDTAGA-peptide conjugate, is dissolved in a mixture of TFA/methanesulfonic acid/TIS/water/dodecanethiol (or 2,2-ethylenedioxide-diethanethiol) (20 ml, 18:0.5:0.5:0.5:0.5) and stirred for ca. 4 hr at 40 C and then poured into ether giving a white precipitate. The precipitate is isolated by filtration and washed with ether (2×20 mL) The crude CDTAGA-peptide ligand conjugate is purified by reverse phase preparative HPLC on a phenomenex C-5 Luna column using a gradient of 5% mobile phase A (0.1% TFA in water) to 25% mobile phase B (0.1% TFA in acetonitrile) over 20 minutes, and held at 25% B for 10 minutes. The fractions of pure peptide are pooled and lyophilized to give the final peptide chelate conjugate. Purity and identity are confirmed by LC/MS.

Chelation:

The purified peptide ligand conjugate is dissolved in H$_2$O (20 ml/g peptide conjugate) and the pH adjusted to 6-7 with a 1 N NaOH solution. Solid MnCl$_2$. 4H$_2$O (1.1×N primary amines×0.05 mmol peptide) is dissolved in water (ca 1 ml/100 mg) and added at RT. The pH is re-adjusted to 6-7 with 1.0 N NaOH. The reaction can be complete in 2-4 hrs, but can also be stirred overnight. The chelation reaction is checked by LC-MS to ensure that it has gone to completion, usually resulting in a cloudy suspension. A solution of 100 mM EDTA (to scavenge the excess manganese ions) is added dropwise with stirring, pH is maintained at 6-7 during EDTA addition.

Purification:

The crude product is purified by preparative HPLC (Phenomenex C-5 Luna, water/ACN 10% water to 30% Acentonitrile over 30 minutes. Fractions are pooled, lyophilized and the purified product analyzed by LC-MS.

C. Synthesis of Compound ID No. 1.

See reaction scheme shown in FIG. 14. Peptide, SEQ ID No. 1 (1.05 mmol) is dissolved in 50 mL of DMF. t-butyl protected CDTAGA-pentafluorophenyl ester (3.8 mmol) is added and DIEA added to adjust the pH to 7.0. After reaction at room temperature overnight, the reaction is triturated with brine (200 mL) and washed with water, and partially dried on filter. The crude wet solid is dissolved in a 60 mL mixture of TFA:methane sulfonic acid:TIS:water:2,2-diethylinedioxy-diethane thiol (55:1:1:2:1) and stirred for 2-3 hours at 40 C. The deprotected ligand, Compound ID No. 5, is obtained after precipitation with diethyl ether. The crude solid is then taken up in 60 mL water and purified by preparatory HPLC, using phenomenex C-5 Luna column using a gradient of 5% mobile phase A (0.1% TFA in water) to 25% mobile phase B (0.1% TFA in acetonitrile) over 20 minutes, and held at 25% B for 10 minutes. The fractions of pure compound are pooled and lyophilized to give the final peptide moiety, purity and identity confirmed by LC/MS (20-50% yield).

The solid is dissolved in ca. 40 mL water and neutralized by addition of 1 M NaOH until the pH is 6.5. Solid MnCl$_2$. 4H$_2$O (317 mg, 1.6 mmol) is dissolved in ca. 5 ml water and added at RT. The pH is re-adjusted to 6.5 with 1.0N NaOH.

The solution is stirred overnight and the resultant solution is cloudy. $Na_2H_2EDTA$ solution (0.1 M) is added dropwise with stirring. The pH is maintained at 6-7 with 1.0 N NaOH The resultant clear solution is purified by preparative HPLC (Phenomenex C5 Luna, water and ACN gradient and the product, eluted at 28-32% ACN. The product Compound ID No. 1 is lyophilized leaving 1.6 g of white powder which is analyzed by LC-MS and gives the correct mass.

The following additional compounds are synthesized by derivatizing the collagen binding peptide with MnCDTAGA using the following general procedure:

2. Compound ID No. 2 is prepared using peptide SEQ ID No. 2 following the general procedure above to give 10 mg of product with the correct molecular mass. The C-terminus is capped with an —$NH_2$ amide and MnCDTAGA is linked to the peptide terminal nitrogen and lysine epsilon amino groups through an amide bond.

3. Compound ID No. 3 is prepared using peptide SEQ ID No. 3 following the general procedure above to give 9.5 mg of product with the correct molecular mass. The C-terminus is capped with an —$NH_2$ amide and MnCDTAGA is linked to the peptide terminal nitrogen and lysine epsilon amino groups through an amide bond.

4. Compound ID No. 4 is prepared using peptide SEQ ID No. 4 following the general procedure above to give 1 mg of product with the correct molecular mass. The C-terminus is capped with an —$NH_2$ amide and MnCDTAGA is linked to the peptide terminal nitrogen or lysine epsilon amino groups through an amide bond.

Relaxivity of Compound ID Nos. 1, 2, and 4

The relaxivity of Compound ID Nos. 1, 2 and 4 are determined in PBS at 37° C. using a Bruker mq60 spectrometer operating at 60 MHz (1.4 tesla). Samples are equilibrated at concentrations ranging from 0-200 μM for at least 30 minutes at 37° C. $T_1$ is measured using an inversion recovery sequence. Relaxivities are calculated by subtracting the relaxation rate of the buffer with Mn from the relaxation rate of the buffer sample with Mn and then dividing the result by the concentration of Compound.

Collagen Binding Properties of Compounds of the Invention

Preparation of Human Collagen:

10 ml of a solution of 3 mg/ml of human type I collagen (VitroCol solution, Advanced Biomatrix, cat#5007-A) is dialyzed against 10 mM Phosphate ($NaH_2PO_4$), pH 4.2 at 4° C. with three changes of the dialysis buffer. The protein concentration is determined by liquid chromatography determination of hydroxyproline (P. Hutson, *J. Chromatogr. B*, 791 (2003) 427-430).

Preparation of Rat Collagen:

10 ml of a 3.79 mg/mL solution of rat collagen (acid soluble, type I, rat tail, Millipore Inc, cat#08-115) is dialyzed against 10 mM Phosphate ($NaH_2PO_4$), pH 4.2 at 4° C. with three changes of the dialysis buffer.

Preparation of Canine Collagen:

Canine collagen (Native canine Collagen Type I and III protein, YO protein AB, cat#739) is dissolved in 0.5 M acetic acid at 3.3 mg/ml by vortexing and shaking overnight at 4° C. The solution is then dialyzed against 10 mM Phosphate ($NaH_2PO_4$), pH 4.2 at 4° C. with three changes of the dialysis buffer.

Preparation of Microtiter Plate:

Ice-cold 1×PBS pH 10.8 is added to the collagen solution for a final collagen concentration of 10 μM, pH 7.4. Collagen solutions are gelled and dried down in the wells of a 96 well microtiter plate (Corning Polystyrene Flat Bottom, cat#3641). 70 μl of 10 μM collagen is aliquoted into each well in every other lane in the plate (48 wells) and the plate is incubated at 37° C. for 18 hours to form a gel and evaporate to dryness. Ungelled collagen is removed by washing the collagen films with 200 μl 1×PBS pH 7.4 (four times, 15 min per wash). The thin collagen fibril film remains, coating the bottom of each well. After washing by PBS the plate is again dried at 37° C. for 2 hours and is stored at −20° C. The final well content of gelled collagen is measured by determination of hydroxyproline and is around 180 μg/ml.

Collagen Binding Assay:

a serial dilution of 0.2 μM-30 μM of the peptide chelate is prepared in PBS, pH 7.4 (~300 μL of solution for each concentration). 90 μl of each concentration is also reserved in a HPLC glass vial as a sample to measure the total concentration. 140 μL of each dilution of peptide chelate is added to wells containing and non-containing collagen (control for nonspecific platic binging). The plate is then incubated on a shaker table (300 rpm) for 2 hours at room temperature to allow the compound to bind. After 2 hours the supernatant from each well (with or without collagen) is transferred to an HPLC glass vial. The concentration of free, unbound compound in the sample supernatants and the concentration of compound in the reserved (total) sample are determined by ICP-MS (Agilent 7500, manganese concentration). The concentration of compound bound to collagen is determined as [bound]=[total]−[unbound].

Collagen binding constant: The binding of compounds to human, rat and dog collagen (5 μM) is measured over the concentration range 0.2-5 μM of Comp ID Nos.: 1-4. The binding data are fit to a model of 1 binding site.

Pharmacokinetics (Rat)

Compound ID No. 1 is formulated at pH 7.5 (TRIS buffer) and administered to Sprague Dawley rats (n=2) at dose of 1.3 umol/kg using a bolus IV injection. Plasma is sampled at 2, 5, 15, 30, and 90 minutes post-injection and analyzed for manganese content using ICP-MS. The pharmacokinetic profile is characterized by a rapid initial blood clearance.

Uptake into Fibrotic Myocardial Tissue

The uptake of Compound ID Nos. 1, 2 and 4 into myocardial fibrotic tissue is determined in a rat model of healed myocardial infarction by comparing uptake in normal vs. scarred myocardium. The collagen binding peptide chelate conjugates have greater binding in fibrotic cardiac tissue as compared with normal myocardial tissue Myocardial infarction is induced in Sprague Dawley rats by occlusion of the left anterior descending coronary artery followed by reperfusion. The rats are anesthetized with an intraperitoneal (i.p.) injection of 100 μg pentobarbital sodium per gram body weight and a thorocotamy is performed. The pericardium is removed and the left anterior artery is sutured with a 7.0 silk suture for 60 minutes after which reperfusion is established.

Compound ID Nos. 1, 2, and 4 are injected into separate animals 3 weeks following infarction at a dose of ~1 umol/kg. Animals are sacrificed at 60 minutes post-injection and the heart removed and sectioned for analysis. Tissue samples from normal myocardium and infarcted myocardium are analyzed for manganese and hydroxyproline (collagen) content.

There is a linear relationship between manganese concentration and collagen tissue content (measured by assessing hydroxyproline concentration) for all compounds tested. As the concentration of collagen in tissue increases the concentration of collagen binding peptide chelate conjugate compound should also increase. The slope for this correlation is a measure of efficacy. Compounds exhibiting a greater slope for collagen vs. concentration of collagen binding peptide chelate conjugate compound will exhibit a greater dynamic range for imaging fibrosis and the higher slope will translate into the ability to more accurately stage fibrosis.

Myocardial Perfusion Imaging

To mimic severe ischemia, a canine model is used in which an inflatable variable vascular occluder is placed around the left anterior descending coronary artery (LAD) to allow occlusion and reperfusion. Imaging is performed on a 3T clinical scanner 4 days after implantation of the occluder. The conventional saturation recovery pulse sequence for stress perfusion imaging is compared with a segmented inversion method. The purpose of the segmented inversion method is to leverage the steady-state properties of Compound ID No. 1. This segmented inversion recovery pulse sequence provides greater T1 weighting, higher spatial resolution, and greater myocardial tissue contrast. Additionally, since imaging is delayed, the entire heart can be imaged. After baseline MRI scanning, the balloon is inflated. Compound ID No. 1 is administered as an i.v. bolus at a dose of 7.5 µmol/kg one minute after coronary artery occlusion. The occlusion is maintained for an additional 4 minutes, after which blood flow is restored. Imaging is performed prior to occlusion release and at multiple time points following reperfusion.

To assess relative perfusion, labeled microspheres are administered at 3 timepoints in the study. La-labeled microspheres are given before coronary artery occlusion, Au-labeled microspheres are given during coronary artery occlusion, and Lu-labeled microspheres are given after reperfusion. In addition, prior to euthanasia, the variable occluder is re-inflated and fluorescent microspheres are administered in combination with KCl to arrest the heart and visually delineate the area of hypo-perfusion. The animal is sacrificed at ca. 120 minutes post Compound ID No. 1 and the heart removed and sectioned according to American Heart Association guidelines (MD Cerqueira et al, Circulation, 2002, 105:539-42). At autopsy under ultraviolet light, the hypo-perfused myocardium is differentiated from normal myocardium due to the lack of fluorescence in the hypo-perfused tissue. Based on the fluorescence, a sample of the ischemic territory and a sample of the remote myocardium are taken for ex vivo analysis. These tissue samples are weighed, digested in nitric acid, and analyzed for the elements La, Au, Lu (the three microsphere injections) and manganese (Compound ID No. 1) using ICP-MS. Concentrations in the ischemic tissue are compared to that of the remote myocardium to assess regional flow and probe uptake.

The myocardial perfusion defect is readily visualized following administration of Compound ID No. 1. Prior to Compound ID No. 1 injection, the myocardium and ventricles are both dark. Ten minutes after injection the ventricles are hyperintense because of contrast agent in the blood and the myocardial perfusion defect (ischemic area) is visualized as a dark zone (orange arrow) while the normal myocardium is seen with bright signal. At 20 minutes, the signal in the blood has decreased but the myocardium remains dark in the ischemic zone and brighter in normal myocardium.

Data are quantitatively evaluated at pre-contrast, at 6 minutes post-contrast, and 15 minutes post-contrast using signal-to-noise ratios (SNR) for normally perfused myocardium, SNR for hypo-perfused myocardium, and contrast to noise ratio (CNR) for normal-to-hypoperfused myocardium.

Reduction in flow is verified by microspheres administered through the left atrial catheter during occlusion. (Spuentrup, et al., Circulation, 2009, 1768-75). The concentration of Mn in the ischemic tissue is lower that the value in the normal myocardium. Thus, even with ~2 hours available for redistribution, Compound ID No. 1 shows preferential deposition in normal vs ischemic cardiac tissue.

Compound ID No. 1 provides MR images reflective of perfusion in the myocardium. The collagen targeted contrast agent provides positive image contrast in the normally perfused myocardium, whereas the ischemic part of the myocardium is hypointense (dark).

Myocardial Fibrosis Imaging

An experimental protocol is developed to test the ability of Compound ID No. 1 to differentiate acute from chronic myocardial infarction in an in-vivo large animal (canine) model. In this model, early following acute myocardial infarction, pathologic fibrosis has not fully developed within the infarct zone (fibrosis-poor), whereas in chronic MI (~8 weeks following MI), dense fibrosis fully replaced necrotic myocardium (fibrosis-rich).

In the myocardial fibrosios canine model, a vascular occluder is placed surgically around the left anterior descending coronary artery (LAD) to allow occlusion and reperfusion. Two animals are studied following acute MI and two additional animals are studied both following acute MI, and chronically at 8 weeks. The LAD vessel is completely occluded for 70-90 minutes and then released to allow reperfusion. The chest is sutured closed, and the animal is allowed to recover. Imaging is performed on a 3T clinical scanner in an acute (<1 week, minimal fibrosis expected in acute necrosis) and chronic (8 weeks, healing complete, necrotic myocardium replaced by dense collagenous scar) time point after infarction. For each time point, the animals undergo 2 scans separated by 48 hours with conventional gadolinium contrast (0.2 mmol/kg GdDTPA) and Compound ID No. 1 (0.0075 mmol/kg).

Imaging Parameters

Imaging is performed on a 3T clinical scanner. Breath holding is achieved by temporarily turning off the animal ventilator, and all images are ECG gated. Standard short and long axis cine imaging is performed throughout the left ventricle to identify left ventricular function and regional wall motion abnormalities. Delayed enhancement imaging (segmented 2D inversion recovery gradient echo) is performed prior to and serially following Compound ID No. 1 administration. Two strategies are employed: (1) a fixed inversion time is chosen to null pre-contrast myocardium (TI~650 ms), and (2) a variable inversion time set to null post-contrast myocardium as is performed in traditional delayed enhancement imaging.

After imaging, animals are euthanized and post mortem analysis of myocardium is performed. Tissue is assessed grossly by histopathologic staining with triphenyltetrazolium chloride for myocardial infarction, and microscopically with Masson's trichrome staining for fibrosis. Additionally quantitative tissue analysis for hydroxyproline is used to measure total collagen content in tissue and compared to tissue manganese concentration by inductively coupled plasma-mass spectrometry. MR data is analyzed quantitatively for conspicuity of infarction and image quality as well as contrast to noise ratio (CNR) for infarct-normal myocardium and infarct-blood.

Histopathologic Comparison

Masson Trichrome stain of tissue taken from infarcted and normal myocardium in both acute and chronic infarcts showed almost no staining for collagen (blue) within the acute infarct tissue, while chronic infarct showed dense fibrotic replacement of necrosis. The concentration of manganese (Compound ID No. 1) and hydroxyproline (collagen) is measured in samples of healthy, ischemic, and infarcted heart tissue. The hydroxyproline concentration is slightly elevated in infarcted tissue compared to remote tissue for the animals with acute infarcts. Conversely, in the chronic infarcts which showed dense scar on Masson Trichrome stain, the hydroxyproline is strongly elevated in the infarcted tissue compared to remote tissue. Since the MM signal enhancement by the imaging probe Compound ID No. 1 is proportional to its concentration, these data show that Compound ID No. 1 enhanced imaging will enable quantitation of organ fibrosis.

Uptake into Fibrotic Liver Tissue

Bile duct ligated (BDL) rats are selected to assess the uptake of the complexes in fibrotic liver tissue as compared to sham operated animals. In this model, the common bile duct is surgically tied off and the resultant cholestasis results in fibrosis around the bile ducts. Laparotomy is performed in Sprague-Dawley rats with double ligation of the common bile duct with a section between the two ligatures (2-3% isoflurane anesthesia). Laparotomy without ligation is also performed as a sham control and to verify that the operation does not alter hepatic function. Fibrosis is evident 15 days after ligation and increases with time up to 30 days after ligation, providing defined endpoints for imaging of moderate and severe fibrosis.

Studies are conducted by injecting Compound ID. No. 1 at a dose ~7.5 μmol/kg. After 90 min, the animals are sacrificed and the 4 liver lobes and abdominal muscle are removed and the manganese concentration quantified by ICP-MS and collagen content quantified using hydroxyproline concentration. The data are consistent with uptake of Compound ID No. 1 into fibrotic-rich liver tissue.

A number of embodiments have been described. Nevertheless, it will be understood that various modifications may be made without departing from the spirit and scope of the invention. Accordingly, other embodiments are within the scope of the following claims

What is claimed is:
1. A compound (Compound ID No. 5) having the following structure:
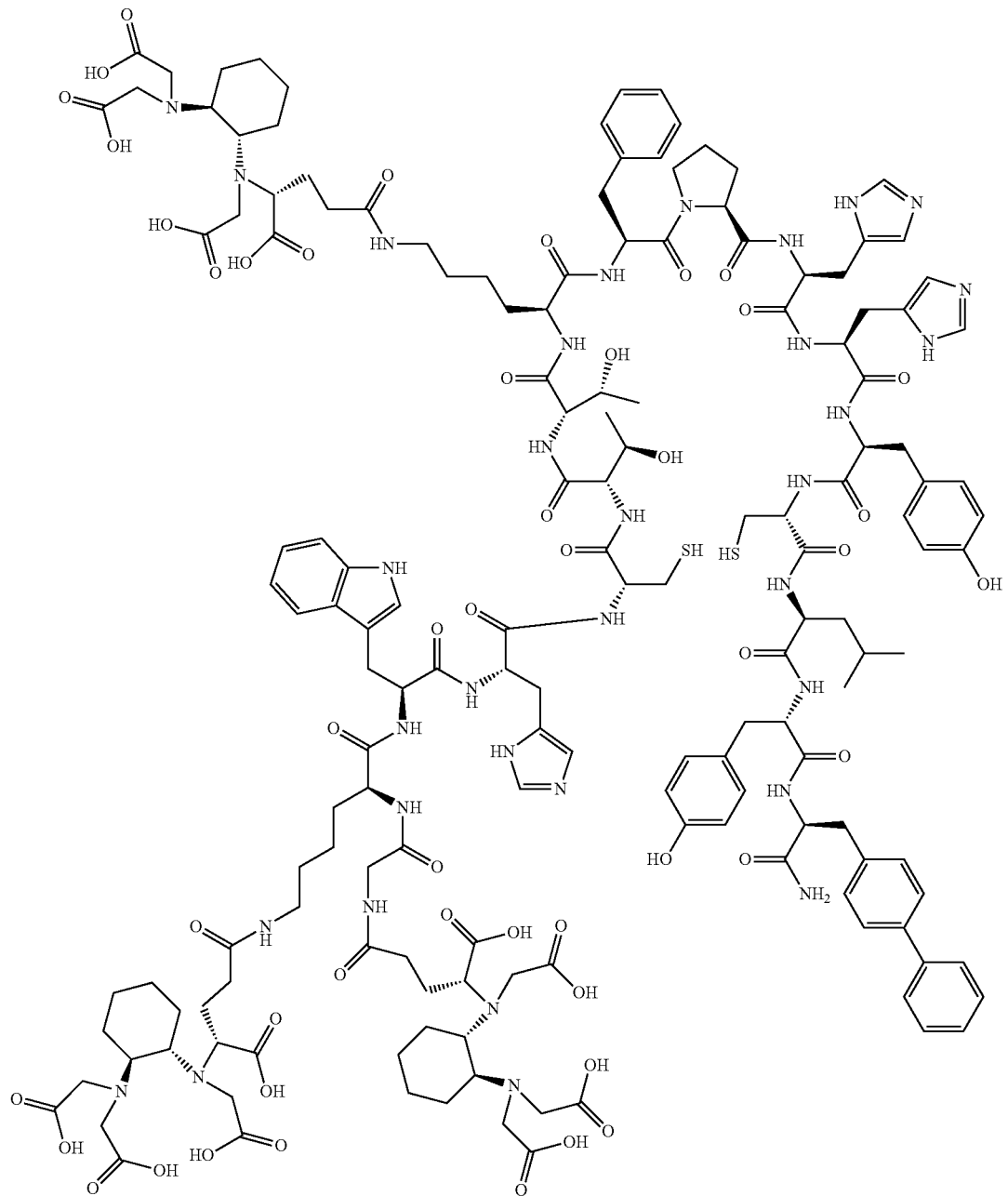
or a pharmaceutically acceptable salt thereof.

2. A compound (Compound ID No. 9) having the following structure:

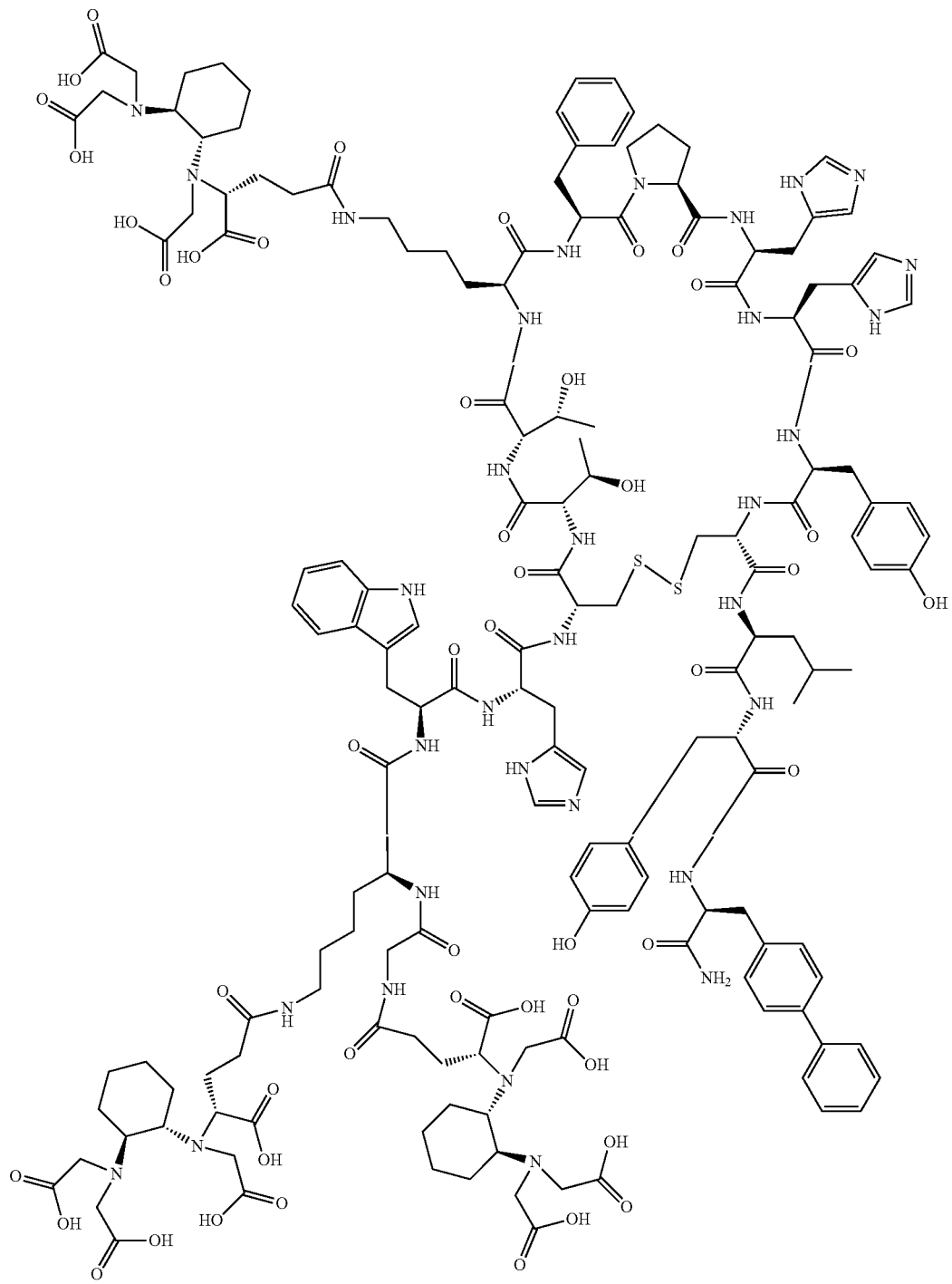

or a pharmaceutically acceptable salt thereof.

3. The compound of claim 1, wherein said compound is complexed to one or more paramagnetic metal ions.

4. The compound of claim 3, wherein said one or more paramagnetic metal ions is selected from the group consisting of: Gd(III), Fe(III), Mn(II), Mn(III), Cr(III), Cu(II), Dy(III), Ho(III), Er(III), Pr(III), Eu(II), Eu(III), Tb(III), and Tb(IV).

5. The compound of claim 4, wherein said paramagnetic metal ion is Mn(II).

6. The compound of claim 2, wherein said compound is complexed to one or more paramagnetic metal ions.

7. The compound of claim 6, wherein said one or more paramagnetic metal ions is selected from the group consisting of: Gd(III), Fe(III), Mn(II), Mn(III), Cr(III), Cu(II), Dy(III), Ho(III), Er(III), Pr(III), Eu(II), Eu(III), Tb(III), and Tb(IV).

8. The compound of claim 7, wherein said paramagnetic metal ion is Mn(II).
9. A compound (Compound ID No. 1) having the following structure:
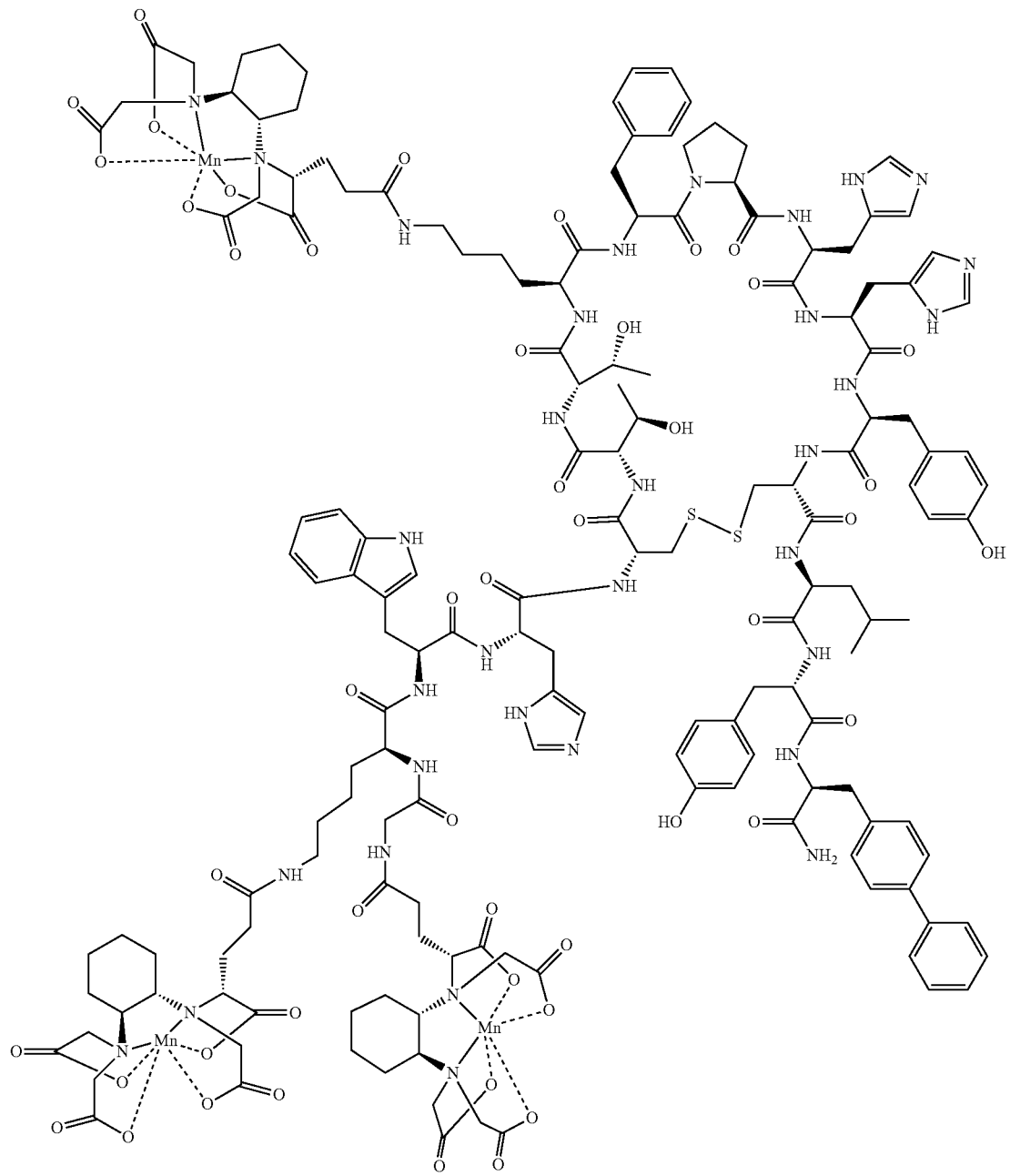
or a pharmaceutically acceptable salt thereof.
10. The compound of claim 9, wherein the pharmaceutically acceptable salt is sodium.
* * * * *

```
                              SEQUENCE LISTING

<160> NUMBER OF SEQ ID NOS: 4

<210> SEQ ID NO 1
   <211> LENGTH: 16
   <212> TYPE: PRT
   <213> ORGANISM: Artificial Sequence
   <220> FEATURE:
   <223> OTHER INFORMATION: synthetic peptide

<400> SEQUENCE: 1

Gly Lys Trp His Cys Thr Thr Lys Phe Pro His His Tyr Cys Leu Tyr
   1               5                   10                  15

<210> SEQ ID NO 2
   <211> LENGTH: 15
   <212> TYPE: PRT
   <213> ORGANISM: Artificial Sequence
   <220> FEATURE:
   <223> OTHER INFORMATION: synthetic peptide

<400> SEQUENCE: 2

Lys Trp His Cys Thr Thr Lys Phe Pro His His Tyr Cys Leu Tyr
   1               5                   10                  15

<210> SEQ ID NO 3
   <211> LENGTH: 16
   <212> TYPE: PRT
   <213> ORGANISM: Artificial Sequence
   <220> FEATURE:
   <223> OTHER INFORMATION: synthetic peptide

<400> SEQUENCE: 3

Lys Tyr Trp His Cys Thr Thr Lys Phe Pro His His Tyr Cys Leu Tyr
   1               5                   10                  15

<210> SEQ ID NO 4
   <211> LENGTH: 15
   <212> TYPE: PRT
   <213> ORGANISM: Artificial Sequence
   <220> FEATURE:
   <223> OTHER INFORMATION: synthetic peptide

<400> SEQUENCE: 4

Lys Trp His Cys Tyr Thr Lys Phe Pro His His Tyr Cys Val Tyr
   1               5                   10                  15
```